United States Patent
He et al.

(10) Patent No.: US 8,846,855 B2
(45) Date of Patent: Sep. 30, 2014

(54) CONJUGATED FUSED THIOPHENES, METHODS OF MAKING CONJUGATED FUSED THIOPHENES, AND USES THEREOF

(71) Applicants: Mingqian He, Horseheads, NY (US); Jianfeng Li, Lake St. Louis, MO (US); James Robert Matthews, Painted Post, NY (US); Weijun Niu, Painted Post, NY (US); Arthur L Wallace, Painted Post, NY (US)

(72) Inventors: Mingqian He, Horseheads, NY (US); Jianfeng Li, Lake St. Louis, MO (US); James Robert Matthews, Painted Post, NY (US); Weijun Niu, Painted Post, NY (US); Arthur L Wallace, Painted Post, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 13/660,529

(22) Filed: Oct. 25, 2012

(65) Prior Publication Data
US 2013/0109821 A1    May 2, 2013

Related U.S. Application Data

(60) Provisional application No. 61/553,331, filed on Oct. 31, 2011.

(51) Int. Cl.
C08G 75/00 (2006.01)
C08G 75/06 (2006.01)
C07D 495/22 (2006.01)

(52) U.S. Cl.
CPC .......... C07D 495/22 (2013.01); C08G 75/06 (2013.01)
USPC .......... 528/377; 528/378; 528/380; 528/370; 528/375; 528/376; 526/204; 526/216; 526/241; 526/256; 526/259; 524/547; 524/548

(58) Field of Classification Search
USPC ................. 528/377, 378, 380, 370, 375, 376
See application file for complete search history.

(56) References Cited

U.S. PATENT DOCUMENTS

| | | | |
|---|---|---|---|
| 7,838,623 B2 | 11/2010 | He | |
| 7,932,344 B2 | 4/2011 | Li | |
| 2005/0082525 A1* | 4/2005 | Heeney et al. | 257/40 |
| 2007/0161776 A1* | 7/2007 | He | 528/373 |
| 2009/0065878 A1 | 3/2009 | Li | |
| 2010/0305288 A1 | 12/2010 | He et al. | |
| 2011/0040042 A1 | 2/2011 | He et al. | |
| 2011/0098478 A1* | 4/2011 | He et al. | 548/105 |
| 2012/0035375 A1 | 2/2012 | He et al. | |

FOREIGN PATENT DOCUMENTS

| | | |
|---|---|---|
| WO | 2006031893 | 3/2006 |
| WO | 2008106019 | 9/2008 |
| WO | 2009123695 | 10/2009 |
| WO | 2011025455 | 3/2011 |

OTHER PUBLICATIONS

Sirringhaus, H. et al., Two-dimensional charge transport in self-organized, high-mobility conjugated polymers, D.M. Nature 1999, 401, 685.

(Continued)

*Primary Examiner* — Shane Fang
(74) *Attorney, Agent, or Firm* — Jason A. Barron

(57) ABSTRACT

Described herein are compositions including heterocyclic organic compounds based on fused thiophene compounds, polymers based on fused thiophene compounds, and methods for making the monomers and polymer along with uses in thin film-based and other devices.

14 Claims, 19 Drawing Sheets

R = alkyl group having at least 4 carbons
Z = terminus of carboxylate

(56) References Cited

OTHER PUBLICATIONS

Allard, S. et al., Organic Semiconductors for Solution-Processable Field-Effect Transistors (OFETs)Angew. Chem. Int. Ed. 2008, 47, 4070.

Katz, H. E., Recent Advances in Semiconductor Performance and Printing Processes for Organic Transistor-Based Electronics, Chem. Mater. 2004, 16, 4748.

He, M. et al., Synthesis and Structure of Alkyl-Substituted Fused Thiophenes Containing up to Seven Rings; J. Org. Chem, 2007, 2, 444.

Fong, H. H. et al., Tetrathienoacene Copolymers As High Mobility, Soluble Organic Semiconductors; J. Am. Chem. Soc. 2008, 130, 13202.

He, M. et al., Alkylsubstituted Thienothiophene Semiconducting Materials; Structure—Property Relations; J. Am. Chem. Soc 2009, 131, 11930.

Bronstein, H. et al., Thieno[3,2-*b*]thiophene—Diketopyrrolopyrrole-Containing Polymers for High_performance Organic Field-Effect Transistors and Organic Photovoltaic Devices; J. Am. Chem. Soc. 2011, 133, 3272.

Li, Y., A High Mobility P-Type DPP-Thieno[3,2-*b*]thiophene Copolymerfor Organic Thn-Film Transistors; Adv. Mater. 2010, 22, 4862-4866.

Tieke, B., Conjugated Polymers Containing Diketopyrrolopyrrole Units in the Main Chain; Beilstein J. Org. Chem. 2010, 6, 830.

\* cited by examiner

R = alkyl group having at least 4 carbons
Z = terminus of carboxylate

R = alkyl group having at least 4 carbons
Z = terminus of carboxylate

R = alkyl group having at least 4 carbons
Z = terminus of carboxylate

R = alkyl group having at least 4 carbons

Hex = n-hexyl, C$_6$H$_{13}$
Dec = n-decyl, C$_{10}$H$_{21}$

CONJUGATED FUSED THIOPHENES, METHODS OF MAKING CONJUGATED FUSED THIOPHENES, AND USES THEREOF

This application claims the benefit of priority under 35 U.S.C. §119 of U.S. Provisional Application Ser. No. 61/553,331 filed on Oct. 31, 2011, the content of which is relied upon and incorporated herein by reference in its entirety.

BACKGROUND

1. Field

Described herein are compositions including heterocyclic organic compounds. More specifically, described herein are fused thiophene compounds, methods for making them, and uses thereof.

2. Technical Background

Highly conjugated organic materials are currently the focus of great research activity, chiefly due to their interesting electronic and optoelectronic properties. They are being investigated for use in a variety of applications, including field effect transistors (FETs), thin-film transistors (TFTs), organic light-emitting diodes (OLEDs), electro-optic (EO) applications, as conductive materials, as two photon mixing materials, as organic semiconductors, and as non-linear optical (NLO) materials. Highly conjugated organic materials may find utility in devices such as RFID tags, electroluminescent devices in flat panel displays, and in photovoltaic and sensor devices.

Materials such as pentacene, poly(thiophene), poly(thiophene-co-vinylene), poly(p-phenylene-co-vinylene) and oligo(3-hexylthiophene) have been intensively studied for use in various electronic and optoelectronic applications. More recently, fused thiophene compounds have been found to have advantageous properties. For example, bisdithieno[3,2-b:2',3'-d]thiophene (1, j=2) has been found to efficiently π-stack in the solid state, possesses high mobility (up to 0.05 cm$^2$/V·s), and has a high on/off ratio (up to 10$^8$). Oligomers and polymers of fused thiophenes, such as oligo- or poly(thieno[3,2-b]thiophene (2) and oligo- or poly(dithieno[3,2-b:2'-3'-d]thiophene) (1)

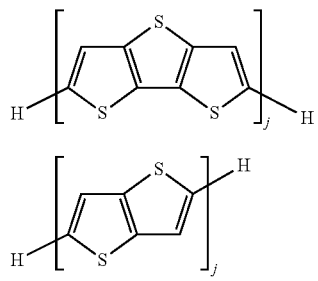

have also been suggested for use in electronic and optoelectronic devices, and have been shown to have acceptable conductivities and non-linear optical properties. However, unsubstituted fused thiophene-based materials tend to suffer from low solubility, marginal processability and oxidative instability. Thus, there remains a need for fused thiophene-based materials having acceptable solubility, processability and oxidative stability.

SUMMARY

Described herein are compositions including heterocyclic organic compounds such as fused thiophene compounds, methods for making them, and uses thereof. The compositions and methods described herein possess a number of advantages over prior art compositions and methods. For example, the fused thiophene compositions described herein can be made to be more soluble and processable than the analogous unsubstituted thiophene compositions. Polymers and oligomers including the fused thiophene moieties described herein can be made to be processable using conventional spin-coating operations. Further, the compositions described herein can be made with substantially no β-H content, greatly improving the oxidative stability of the compositions.

A first aspect comprises a compound comprising the formula 100 or 101:

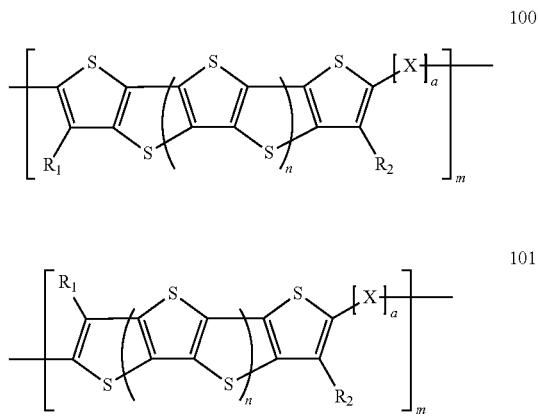

wherein a, m, and n are independently integers of one or greater; each X independently comprises a conjugated group, wherein when a=1, X is not aryl and when a>1, all X are not aryl; and $R_1$ and $R_2$ are, independently, substituted or unsubstituted alkyl, substituted or unsubstituted alkenyl, substituted or unsubstituted alkynyl, aryl, substituted or unsubstituted cycloalkyl, aralkyl, amino, ester, aldehyde, hydroxyl, alkoxy, thiol, thioalkyl, halide, acyl halide, acrylate, or vinyl ether. In some embodiments, at least one of $R_1$ and $R_2$ comprises a substituted or unsubstituted alkyl. In some embodiments, at least one of $R_1$ and $R_2$ comprises an unsubstituted alkyl. In some embodiments, a is 2 or more and X comprises a conjugated alkenyl or alkynyl or aryl. In some embodiments, n is from 1 to 15.

In some embodiments, the compound comprising the formula 100 or 101 further comprises a polymer. In some embodiments, the compound is incorporated into a conjugated fused thiophene polymer or oligomer having m>1. In some embodiments, the polymer has a molecular weight from about 400 to about 1800 Da.

In another aspect, the compound comprising the formula 100 or 101 is incorporated into an electronic, optoelectronic, or nonlinear optical device. In some embodiments, the device comprises a transistor (FET), a thin-film transistor (TFT), an organic light-emitting diode (OLED), an electro-optic (EO) device, a conductive material, a two photon mixing material, an organic semiconductor, a RFID tag, an electroluminescent device, or a photovoltaic and sensor device.

Another aspect comprises method for making a compound comprising formula 100 or 101, comprising the steps of: (i) providing a fused thiophene moiety of structure 1 or 2:

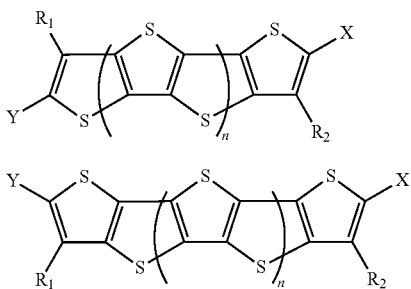

wherein $R_1$ and $R_2$ independently, substituted or unsubstituted alkyl, substituted or unsubstituted alkenyl, substituted or unsubstituted alkynyl, aryl, substituted or unsubstituted cycloalkyl, aralkyl, amino, ester, aldehyde, hydroxyl, alkoxy, thiol, thioalkyl, halide, acyl halide, acrylate, or vinyl ether; and X and Y are independently, halide or $Sn(Alk)_3$, wherein Alk is a substituted or unsubstituted alkyl or substituted or unsubstituted cycloalkyl; (ii) providing a bis-substituted conjugated moiety of structure 3 or 4:

$$Sn(Alk)_3\text{-}Z\text{—}Sn(Alk)_3 \qquad 3$$

$$Ha\text{-}Z\text{-}Ha \qquad 4$$

wherein Z is a conjugated group comprised not solely of an one or more aryl groups, Ha is halogen, and Alk is a substituted or unsubstituted alkyl or substituted or unsubstituted cycloalkyl; (iii) coupling the fused thiophene moiety of structure 1 or 2 with the conjugated moiety of structure 3 or 4 via a catalyzed reaction; wherein compound 3 is used when X and Y are halogen and compound 4 is used when X and Y are $Sn(Alk)_3$. In some embodiments, the catalyzed reaction is a metal catalyzed reaction. In some embodiments, the metal catalyzed reaction is a Stille-type coupling. In some embodiments, the reaction further comprises polymerizing the compound of formula 100 or 101.

Additional features and advantages will be set forth in the detailed description which follows, and in part will be readily apparent to those skilled in the art from the description or recognized by practicing the embodiments as described in the written description and claims hereof, as well as in the appended drawings.

It is to be understood that both the foregoing general description and the following detailed description are merely exemplary, and are intended to provide an overview or framework for understanding the nature and character of the invention.

BRIEF DESCRIPTION OF THE DRAWINGS

The accompanying drawings are included to provide a further understanding of the description, and are incorporated in and constitute a part of this specification. The drawings are not necessarily to scale, and sizes of various elements may be distorted for clarity. The drawings illustrate one or more embodiment(s) and together with the description serve to explain the principles and operation of the embodiments.

DETAILED DESCRIPTION

Figure 1:
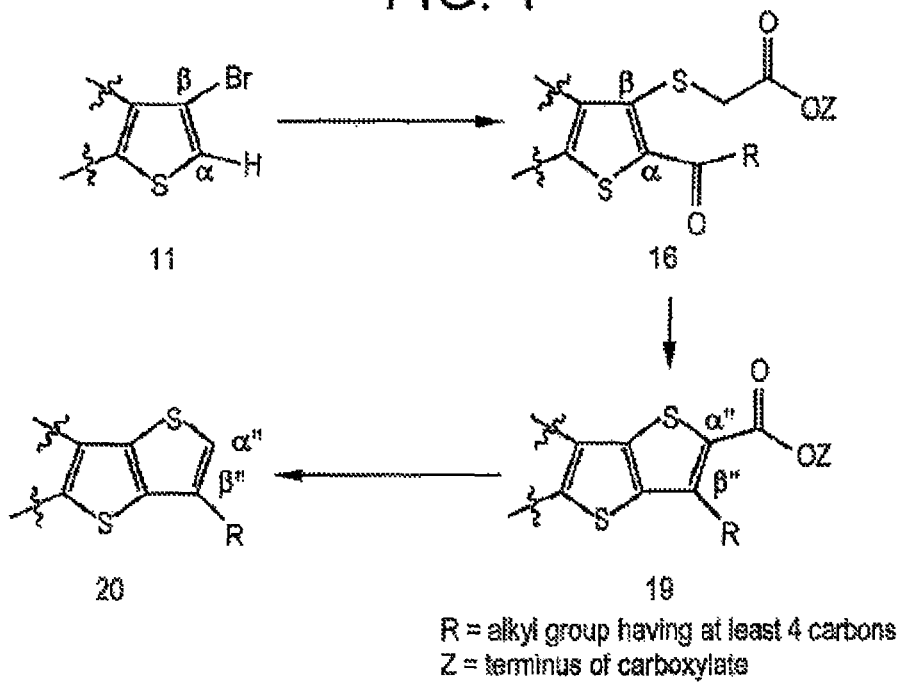
FIG. 1 is a reaction scheme showing a method for making a β"-R-substituted fused thiophene moieties.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

The term "alkyl group" as used herein is a branched or unbranched saturated hydrocarbon group of 1 to 40 carbon atoms, such as methyl, ethyl, n-propyl, isopropyl, n-butyl, isobutyl, t-butyl, pentyl, hexyl, heptyl, octyl, decyl, or tetradecyl, and the like. The alkyl group can be substituted or unsubstituted. The term "unsubstituted alkyl group" is defined herein as an alkyl group composed of just carbon and hydrogen. The term "substituted alkyl group" is defined herein as an alkyl group with one or more hydrogen atoms substituted with a group including, but not limited to, an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, an acyl halide, an acrylate, or a vinyl ether. For example, the alkyl groups can be an alkyl hydroxy group, where any of the hydrogen atoms of the alkyl group are substituted with a hydroxyl group.

The term "alkyl group" as defined herein also includes cycloalkyl groups. The term "cycloalkyl group" as used herein is a non-aromatic carbon-based ring composed of at least three carbon atoms, and in some embodiments from three to 20 carbon atoms. Examples of cycloalkyl groups include, but are not limited to, cyclopropyl, cyclobutyl, cyclopentyl, cyclohexyl, etc. The term cycloalkyl group also includes a heterocycloalkyl group, where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl group" also includes "heteroaryl group," meaning an aromatic ring composed of at least three carbon atoms that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy as defined herein. In some embodiments, the term "aryl group" is limited to substituted or unsubstituted aryl and heteroaryl rings having from three to 30 carbon atoms.

The term "aralkyl" as used herein is an aryl group having an alkyl group as defined above attached to the aryl group. An example of an aralkyl group is a benzyl group.

The term "alkenyl group" is defined as a branched or unbranched hydrocarbon group of 2 to 40 carbon atoms and structural formula containing at least one carbon-carbon double bond.

The term "alkynyl group" is defined as a branched or unbranched hydrocarbon group of 2 to 40 carbon atoms and a structural formula containing at least one carbon-carbon triple bond.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect. In some embodiments, "conjugated groups" is limited to conjugated groups having three to 30 carbon atoms.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In one aspect, described herein are compositions comprising at least one fused thiophene moiety comprising the formula 3 or 4

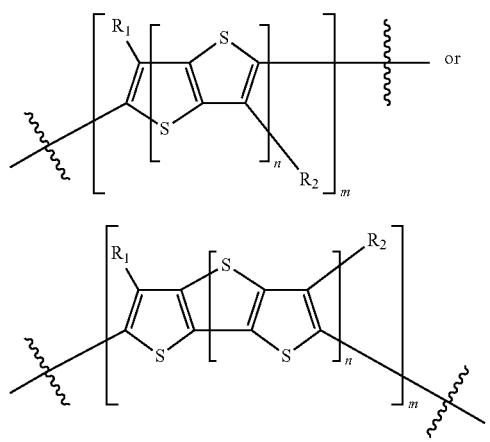

In another aspect, the composition comprising at least one moiety comprising the formula 3' or 4'

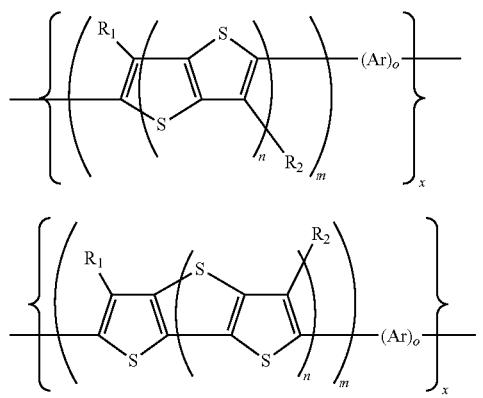

wherein n is an integer greater than zero; in some embodiments, n is an integer of 2 or more; m is an integer greater than zero; in some embodiments, m is an integer of two or more; o is an integer greater than zero; x is an integer greater than or equal to one; $R_1$ and $R_2$ are, independently, hydrogen or an alkyl group, wherein at least one of $R_1$ and $R_2$ is an alkyl group, and Ar is an aryl group, wherein n is not one.

In one aspect, with respect to structures 3, 3', 4, and 4', n is an integer greater than zero; m is an integer greater than 0; $R_1$ and $R_2$ are, independently, hydrogen or an alkyl group, and wherein at least one of $R_1$ and $R_2$ is an alkyl group. As used herein, the fused thiophene ring system of a fused thiophene moiety is the heterocyclic core of the moiety, and does not include the α-substituents and the β-substituents (e.g. $R_1$ and $R_2$) bound to the fused thiophene ring system. For example, the fused thiophene ring systems of structures 3 and 4 having n=1 are shown below as structures 5 and 6, respectively.

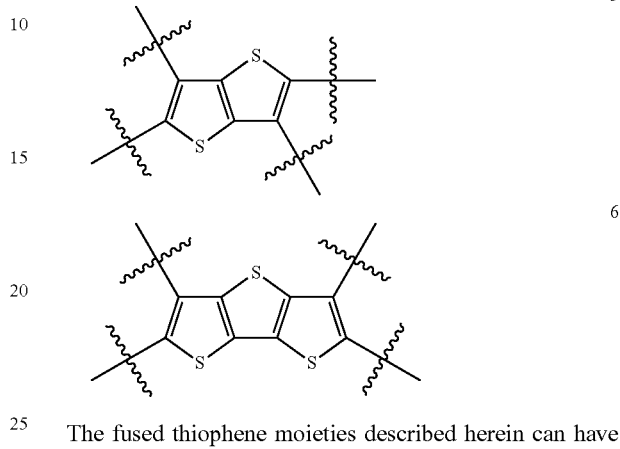

The fused thiophene moieties described herein can have any number of fused rings. For example, the fused thiophene moieties can be bicyclic (3 and 3', n=1); tricyclic (4 and 4', n=1); tetracyclic (3 and 3', n=2); pentacyclic (4 and 4', n=2); hexacyclic (3 and 3', n=3); or heptacyclic (4 and 4', n=3). The methods described herein permit the construction of fused thiophene moieties having any desired number of rings. In some embodiments, n is 1, 2, 3, 4, 5, 6, 7, 8, 9, 10, 11, 12, 13, 14, or 15. In some embodiments, n is 2 or more. In some embodiments, m is 1, 2, 3, 4, 5, 6, 7, 8, 9, 10, 11, 12, 13, 14, or 15. In some embodiments, o is 1, 2, 3, 4, 5, 6, 7, 8, 9, 10, 11, 12, 13, 14, or 15. In some embodiments the fused thiophene moiety can be tricyclic or greater (i.e., 4 or 4', n 1; or 3 or 3', n≥2). In some embodiments, the fused thiophene moiety can be tetracyclic or greater (i.e., 4 or 4', n≥2; or 3 or 3', n≥2).

In another aspect, the composition comprises at least one moiety comprising the formula 3" or 4"

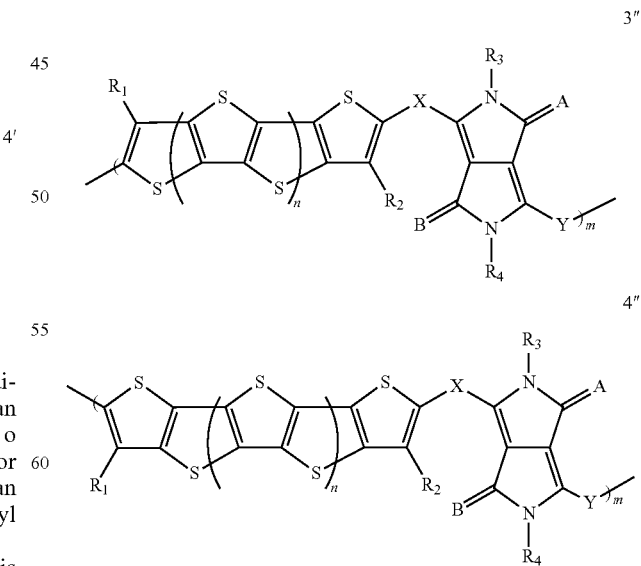

wherein n is an integer of 1 or more; m is an integer of 1 or more; X and Y are independently, a covalent bond or aryl; $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, or vinyl ether; $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, or vinyl ether; and, A and B are, independently, either S or O.

The fused thiophene moieties described in 3" and 4" can have any number of fused rings above 3. For example, the fused thiophene moieties can be tetracyclic (3", n=2); pentacyclic (4", n=2), hexacyclic (3", n=3); or heptacyclic (4", n=3). The methods described herein permit the construction of fused thiophene moieties having any desired number of rings. In one aspect, for 3" and 4", n is 1, 2, 3, 4, 5, 6, 7, 8, 9, 10, 11, 12, 13, 14, or 15.

In another aspect, the composition comprises at least one moiety comprising the formula 100 or 101:

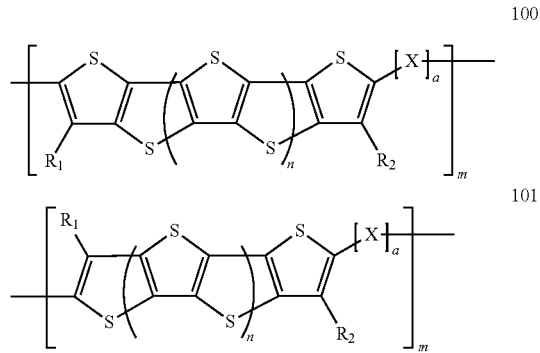

wherein m is an integer of 1 or more; n is an integer of 1 or more; X is a conjugated group, a is an integer of 1 or more; $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, or vinyl ether; $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, or vinyl ether; and, A and B are, independently, either S or O.

The fused thiophene moieties described in 100 and 101 can have any number of fused rings above 3. For example, the fused thiophene moieties can be tetracyclic (100, n=2); pentacyclic (101, n=2), hexacyclic (100, n=3); or heptacyclic (101, n=3). The methods described herein permit the construction of fused thiophene moieties having any desired number of rings. In some embodiments, for 100 and 101, n is 1, 2, 3, 4, 5, 6, 7, 8, 9, 10, 11, 12, 13, 14, or 15. In some embodiments, for 100 and 101, m is 1, 2, 3, 4, 5, 6, 7, 8, 9, 10, 11, 12, 13, 14, or 15. In some embodiments, for 100 and 101, a is 1, 2, 3, 4, 5, 6, 7, 8, 9, 10, 11, 12, 13, 14, or 15.

In some embodiments, X is a conjugated group, wherein when a=1, X is not aryl and when a>1, all X are not aryl. In some embodiments, X is a conjugated group wherein X is not aryl. In some embodiments, X is a combination of one or more linear and one or more cyclic conjugated groups, for example conjugated linear alkyl-conjugated cyclic alkyl-conjugated linear alkyl. In some embodiments, X is a conjugated alkyl group. In some embodiments X is ethynyl or ethylene. In some embodiments, X is a polycyclic heteroaryl, optionally in combination with one or more linear conjugated groups. In some embodiments, X is benzo-1,2,5-thiadiazyl or diketopyrrolopyrrole.

The fused thiophene moieties described herein are substituted at least one of the β-positions of the fused thiophene ring system with an alkyl group. As used herein, an α-position of a fused thiophene ring system is a non-fused carbon center that is directly adjacent to the sulfur of a fused thiophene, while a β-position is a non-fused carbon center that is separated from the sulfur of the fused thiophene by an α-position. In the structures 3, 3', 3", 4, 4', 4", 100, and 101, the α-positions are shown as being connected to the rest of the composition, while the β-positions are substituted with $R_1$ and $R_2$.

In one aspect, at least one of $R_1$ and $R_2$ is an alkyl group. Previously, there have been no methods for producing fused thiophene moieties of structures 3, 3', 3", 4, 4', 4", 100, and 101 having alkyl substitution at the β-positions of the fused thiophene ring system. As described in more detail in the Examples, below, methods conventionally used to alkylate simple unfused thiophenes fail when used in attempts to alkylate fused thiophene ring systems. In one aspect, described herein are methods for making fused thiophene moieties having large alkyl substitution at the β-positions of the fused thiophene ring system.

In one aspect, $R_1$ and $R_2$ can be a variety of substituted or unsubstituted alkyl groups. For example, at least one of $R_1$ or $R_2$ is an unsubstituted alkyl group. In this aspect, the unsubstituted alkyl group can be a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In another aspect, at least one of $R_1$ or $R_2$ is an alkyl group, itself at least four carbons in size, which is substituted. In a further aspect, substitution of the alkyl group is separated from the fused thiophene ring system by at least two carbons. In one aspect, $R_1$ and/or $R_2$ can be substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, acyl halide, an acrylate, or a vinyl ether. Examples of substituted alkyl groups include, but are not limited to, 6-hydroxyhexyl and 3-phenylbutyl. The selection of $R_1$ and $R_2$ will depend on the end use of the fused thiophene moiety-containing composition. The methods described herein permit the synthesis of fused thiophene moieties having a wide variety of $R_1$ and $R_2$ substituents. Any functionality on a substituted alkyl group can be protected in order to survive subsequent reaction steps.

Unsubstituted fused thiophene ring systems (i.e., no substitution at the α- or β-positions) tend to be relatively insoluble. Thus, in one aspect, $R_1$ and $R_2$ can be an alkyl group having at least six carbons in size. For example, the alkyl group can have the formula $C_kH_{2k+1}$, where k is an integer greater than or equal to six.

In certain aspects, the fused thiophene ring system is substituted at both β-positions, so that there are no β-hydrogens on the ring system. For example, in one aspect, neither $R_1$ nor $R_2$ in structures 3, 3', 3", 4, 4', 4", 100, and 101 is H. Such moieties can be incorporated in oligomers and polymers having substantially no β-hydrogen content, and will have increased oxidative stability. For example, the molar ratio of β-hydrogen to fused thiophene ring system can be less than about 1/6, 1/7, 1/8, 1/9, or 1/10. In a further aspect, one or both of $R_1$ and $R_2$ can be an alkyl group. In one aspect, $R_1$ and $R_2$ are identical alkyl groups. When $R_1$ and $R_2$ are identical, regioregular polymers can be easily constructed because the problems of regioselectivity (i.e. head-to-tail vs. head-to-head coupling) of polymerization reactions disappear. In other aspects, $R_1$ and $R_2$ may also be different. For example, $R_1$ can be at least four carbons in size, with $R_2$ being less than four carbons in size (e.g., a methyl group). Alternatively, in another aspect, both $R^1$ and $R^2$ can be at least four carbons in size.

With respect to moieties 3, 3', 3", 4, 4', 4", 100, and 101, an aryl group (Ar) or conjugated group may be attached to the α-position of the fused thiophene moiety.

In one aspect, Ar comprises one or more unfused thiophene groups, one or more fused thiophene groups, or a combination of unfused and fused thiophene groups. For example, the moiety comprises the formula 200 or 201:

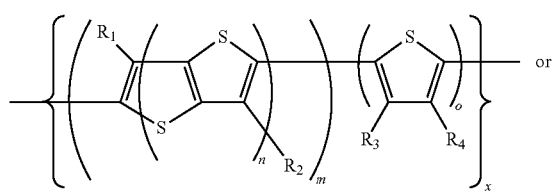

200 or

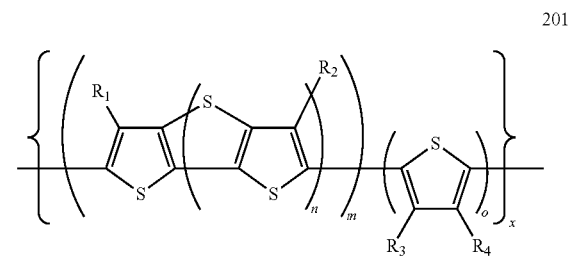

201 wherein o is for more; in some embodiments, o is 1, 2, or 3; and $R_3$ and $R_4$ are, independently, hydrogen or an alkyl group. In some embodiments, n is 2, 3, or 4, and m is 1. In other embodiments, n is 2, 3, or 4; m is one; and o is 1, 2, or 3. In the case when Ar is a fused thiophene, it is contemplated that the fused thiophene can be one fused thiophene group or two or more fused thiophene groups. When Ar is two or more fused thiophene groups, the fused thiophene groups can be the same or different. For example, Ar can be a bis-fused thiophene covalently bonded to a tris-fused thiophene. In other aspects, Ar can be one or more substituted or unsubstituted thiophene groups bonded to a substituted or unsubstituted fused thiophene group.

In another aspect, with respect to moieties 3', 3", 4' and 4", the Ar moiety comprises 300 or 301

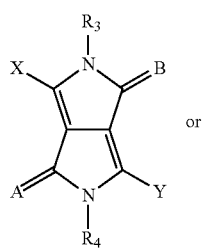

300 or

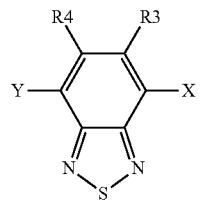

301 wherein A and B are O or S, $R_3$ and $R_4$ are $R_3$ and $R_4$ are, independently, substituted or unsubstituted alkyl, substituted or unsubstituted alkenyl, substituted or unsubstituted alkynyl, aryl, cycloalkyl, aralkyl, amino, ester, aldehyde, hydroxyl, alkoxy, thiol, thioalkyl, halide, acyl halide, acrylate, or vinyl ether, and X and Y are independently covalent bonds or one or more aryl groups, one of which ultimately links to the fused thiophene moiety.

In another aspect, any of the sulfur atoms present in the fused thiophene compounds described herein can be oxidized to produce a $SO_2$ group. In another aspect, a composition includes at least one of the following oxidized fused thiophene moieties:

44

45

In some embodiments, with respect to structures 44 and 45, n is an integer greater than zero; in some embodiments, n is an integer of 2 or greater; m is no less than one; $R_1$ and $R_2$ are, independently, hydrogen or an alkyl group, wherein each T is, independently, S or $SO_2$, wherein T is $SO_2$ in at least one of the central-most rings of the oxidized fused thiophene ring system. Each T is independently S and $SO_2$, where T is $SO_2$ in at least one of the central-most rings of the fused thiophene ring system. As used herein, the central-most ring of a fused thiophene ring system having an odd number 2q+1 of fused rings is the q+1$^{th}$ ring from an end of the ring system. The central-most rings of a fused thiophene ring system having an even number 2q of fused rings are the q$^{th}$ and q+1$^{th}$ rings from an end of the ring system. For example, the central-most ring of a three-ring system is the second ring, the central-most rings of a four-ring system are the second and third rings, and the central-most ring of a five-ring system is the third ring.

In another aspect, the oxidized moiety comprises the formula 44' or 45':

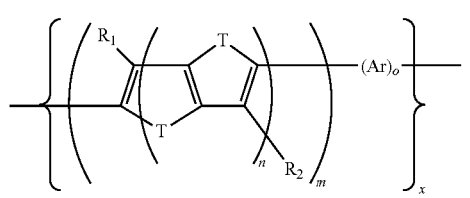

44'

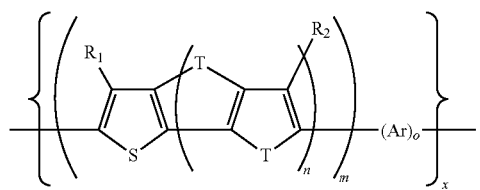

45' wherein T is $SO_2$ in at least one of the central-most rings of the oxidized fused thiophene ring system. In one aspect, T in at least one of the central-most rings is $SO_2$ and the remaining S atoms are not oxidized.

Any of the oxidized fused thiophene compounds described herein can be used in polymers, oligomers, monomers, chromophores, and other compositions as described above. For example, the at least one oxidized fused thiophene moiety can be present in the composition at a total concentration of at least 1 wt %. The value of n can be, for example, 1, 2, 3, 4, or 5. In other aspects, the fused thiophene moiety is tricyclic or greater (i.e., 45', n≥1; or 44', n≥1). In some embodiments, n is 2 or more. In further aspects, at least one of $R_1$ and $R_2$ is an alkyl group at least six carbons in size directly bound to the oxidized fused thiophene ring system core of the oxidized fused thiophene moiety. Both $R_1$ and $R_2$ can be alkyl groups, and can be the same as or different from one another. In certain aspects, neither $R_1$ nor $R_2$ is H. In other aspects, the composition has a ratio of β-hydrogen to oxidized fused thiophene ring systems of less than about 1/10, 1/9, 1/8, 1/7, or 1/6. In one aspect, the oxidized fused compounds have the structure:

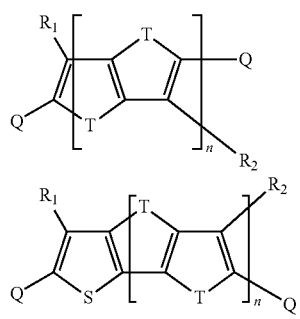

wherein n is an integer greater than zero; $R_1$ and $R_2$ are, independently, hydrogen or an alkyl group, and Q is, independently, hydrogen, a substituted or unsubstituted alkyl group, an acyl halide, an ester, an aldehyde, a ketone, a hydroxyl group, a thiol group or alkyl substituted thiol group, an alkoxy group, an acrylate group, an amino group, a vinyl ether, a hydroxy alkyl group, a carboxylic acid group, or a halide.

Examples of oxidized fused thiophene moieties are shown below as structures 46, 47, 48 and 49:

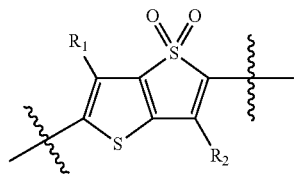

46

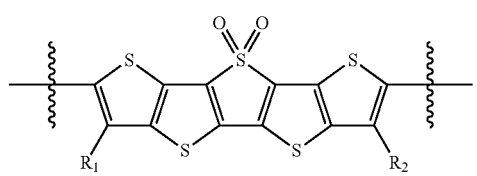

47

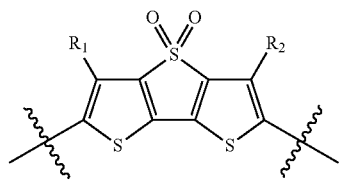

48

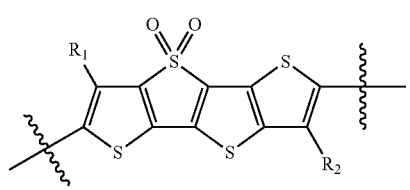

49

The fused thiophene moieties of structures 3, 3', 3", 4, 4', 4", 44', 45', 100, and 101 can exist as simple monomeric fused thiophenes, or can be incorporated into more complex compounds, such as oligomers or polymers. For example, the fused thiophene moieties described in 3 and 4 can be incorporated in simple fused thiophene monomers having the formulae 7 and 8:

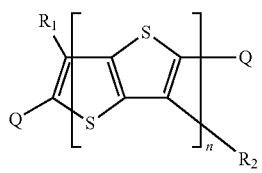

7

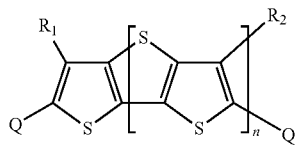

8 wherein n is an integer greater than zero; in some embodiments, n is an integer of 2 or more; $R_1$ and $R_2$ are, independently, hydrogen or alkyl, and Q is, independently, hydrogen, a substituted or unsubstituted alkyl group (e.g., an alkyl hydroxy group), a carboxylic acid, an acyl halide, an ester, an aldehyde, a ketone, a hydroxyl group, a thiol group or alkyl substituted thiol group, an alkoxy group, an acrylate group, an amino group, a vinyl ether, or a halide. In one aspect, each Q in 7 and 8 is bromide. In certain aspects, monomers having structures 7 and 8 can be used to make fused thiophene oligomers and polymers, as described below.

The fused thiophene monomers 7 and 8, or alternatively oxidized fused thiophene monomers 44 and 45, can be incorporated in oligomers and polymers having conjugated homo-oligomeric or homopolymeric blocks of the fused thiophene moieties to produce polymers having the fused thiophene moieties 3, 3', 3", 4, 4', 4", 44', 45', 100, or 101. For example, according to one embodiment, an oligomer or polymer includes a fused thiophene of structure 3, 3', 3", 4, 4', 4", 44', 45', 100, or 101 in which m is greater than 1. In further embodiments, m is at least about four. In another aspect, when the polymer is a homopolymer, m is at least about 10. In this aspect, it is contemplated that the monomers 7 or 8 (or, alternatively 44 or 45) can be polymerized to produce a homopolymer composed of residues having the formula 3 or 4 (or alternatively 44' or 45'). In other aspects, m is from 1 to 10,000, 1 to 9,000, 1 to 8,000, 1 to 7,000, 1 to 6,000, 1 to 5,000, 1 to 4,000, 1 to 3,000, 1 to 2,000, 1 to 1,000, 1 to 500, 1 to 250, 1 to 100, 1 to 50, 1 to 25, 1 to 10, 25 to 1000, 25 to 500, 25 to 250, 50 to 1000, 50 to 500, or 50 to 250.

In other aspects, the fused thiophene monomers described herein (e.g., 7 and 8) can be incorporated into conjugated copolymers with other aromatic or unsaturated moieties. For example, the fused thiophene monomers 7 and 8 (or, alternatively 44 or 45) can be copolymerized with other substituted or unsubstituted fused thiophene moieties to form a conjugated fused thiophene polymer or oligomer. Alternatively, the fused thiophene monomers 7 and 8 (44 or 45) can be copolymerized with substituted or unsubstituted thiophenes to form thiophene/fused thiophene polymers or oligomers. The fused thiophene monomers 7 and 8 (44 or 45) can also be copolymerized with other moieties commonly used in conjugated polymers, such as vinylene, phenylene, or other arylene or heteroarylene moieties.

The fused thiophene moieties described herein can be incorporated into a wide variety of other types of polymers. For example, the fused thiophenes having the formula 7 and 8 (44 or 45) can be incorporated into the main chain of a polymer such as, for example, a polyester, a polyurethane, a polyether, a polyamide, a polycarbonate, or a polyketone; and in the side chain of a polymer such as, for example, a polyacrylate, a polymethacrylate, or a poly(vinyl ether). It is contemplated that the fused thiophenes having the formula 7 and 8 (44 or 45) can be modified with reactive groups (e.g., acyl chloride, alcohol, acrylate, amine, vinyl ether) that will permit the incorporation of the monomer into the polymer. For example, $R^1$, $R^2$, and/or Q can be modified with such reactive groups.

In other aspects, the moieties 3', 3", 4', 4", 44', 45', 100 or 101 can be incorporated in oligomers and polymers having conjugated homo-oligomeric or homopolymeric blocks of the 3', 3", 4', 4", 44', 45', 100 or 101 moieties to produce polymers. For example, according to one embodiment, an oligomer or polymer includes a fused thiophene of structure 3', 3", 4', 4", 44', 45', 100 or 101 in which m is greater than 1. In further embodiments, m is at least about four. In another aspect, when the polymer is a homopolymer, m is at least about 10. In this aspect, it is contemplated that the moieties 3', 3", 4', 4", 44', 45', 100 or 101 can be polymerized to produce a homopolymer. In other aspects, m is from 1 to 10,000, 1 to 9,000, 1 to 8,000, 1 to 7,000, 1 to 6,000, 1 to 5,000, 1 to 4,000, 1 to 3,000, 1 to 2,000, 1 to 1,000, 1 to 500, 1 to 250, 1 to 100, 1 to 50, 1 to 25, 1 to 10, 25 to 1000, 25 to 500, 25 to 250, 50 to 1000, 50 to 500, or 50 to 250.

In some embodiments, the polymers having conjugated homo-monomeric (i.e., single), homo-oligomeric or homopolymeric blocks of the 3', 3", 4', 4", 44', 45', 100 or 101 moieties have molecular weights from about 10 to about 10,000 Da. In some embodiments, the molecular weight of the polymers having conjugated homo-monomeric (i.e., single), homo-oligomeric or homopolymeric blocks of the 3', 3", 4', 4", 44', 45', 100 or 101 moieties have molecular weights from about 10 to about 10,000, about 100 to about 8000, about 200 to about 7000, about 300 to about 6000, about 400 to about 5000, about 500 to about 4000, about 500 to about 3000, about 500 to about 2000, about 500 to about 1500, about 600 to about 1400, about 700 to about 1300, about 800 to about 1200, about 900 to about 1100, or about 100, 200, 300, 400, 500, 600, 700, 800, 900, 1000, 1100, 1200, 1300, 1400, 1500, 1600, 1700, 1800, 1900, 2000, 2500, 3000, 3500, 4000, 5000, 6000, or 7000 Da.

In other aspects, the moieties 3', 3", 4', 4", 44', 45', 100 or 101 can be incorporated into conjugated copolymers with other aromatic or unsaturated moieties. For example, the moieties 3', 3", 4', 4", 44', 45', 100 or 101 can be copolymerized with other substituted or unsubstituted fused thiophene moieties to form a conjugated fused thiophene polymer or oligomer. Alternatively, the moieties 3', 3", 4', 4", 44', 45', 100 or 101 can be copolymerized with substituted or unsubstituted thiophenes to form thiophene/fused thiophene polymers or oligomers. The moieties 3', 3", 4', 4", 44', 45', 100 or 101 can also be copolymerized with other moieties commonly used in conjugated polymers, such as vinylene, phenylene, or other arylene or heteroarylene moieties.

The moieties 3', 3", 4', 4", 44', 45', 100 or 101 described herein can be incorporated into a wide variety of other types of polymers. For example, the moieties 3', 3", 4', 4", 44', 45', 100 or 101 can be incorporated into the main chain of a polymer such as, for example, a polyester, a polyurethane, a polyether, a polyamide, a polycarbonate, or a polyketone; and in the side chain of a polymer such as, for example, a polyacrylate, a polymethacrylate, or a poly(vinyl ether). It is contemplated that the moieties 3', 3", 4', 4", 44', 45', 100 or 101 can be modified with reactive groups (e.g., acyl chloride, alcohol, acrylate, amine, vinyl ether) that will permit the incorporation of the monomer into the polymer.

In another aspect, the fused thiophenes described herein can also be incorporated in donor-acceptor chromophores, such as those commonly used in polymeric electro-optic materials. For example, the fused thiophene moieties of structures 3 and 4 can be incorporated into a donor-acceptor chromophore having the structure 9 or 10:

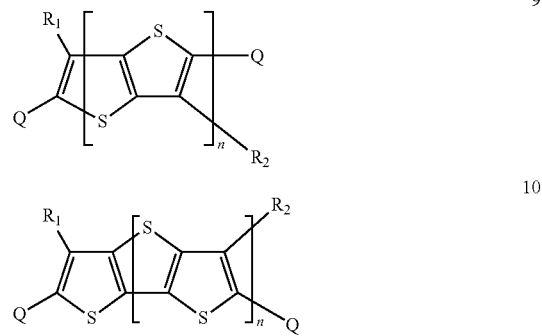

where D is an electron donating group, and A is an electron accepting group. Donor-acceptor chromophores are described in more detail in U.S. Pat. Nos. 6,584,266; 6,514,434; 6,448,416; 6,444,830; and 6,393,190, each of which is hereby incorporated herein by reference in its entirety. In one aspect, the fused thiophene having the formula 7 or 8 can be reacted with an electron donating group and electron accepting group to produce compounds having the formula 9 and 10, respectively.

In various aspects, the compositions described herein have a sufficiently high concentration of the fused thiophene moieties of structures 3 or 4 (or, alternatively 44 or 45) to yield a desired electronic or optoelectronic property to the composition. For example, the compositions have at least one fused thiophene moiety of structures 3 or 4 (or, alternatively 44 or 45) in a total concentration of at least 1 wt %. In a further aspect, the compositions described herein have at least one fused thiophene moiety of structures 3 or 4 (or 44 or 45) in a total concentration of at least 3 wt %. In additional aspects, the composition has at least one fused thiophene moiety of structures 3 or 4 (or 44 or 45) in higher total concentrations of, for example, at least 10 wt %, 20 wt %, 30 wt %, 40 wt %, or 50 wt %. Due to the presence of an alkyl group at the β-position of the fused thiophene ring, the compositions can have higher concentrations of fused thiophene moieties yet remain soluble and processable.

The compositions described herein (monomers, oligomers, polymers) can be used to make a wide variety of devices. For example, the device can be a fused thiophene moiety-containing composition configured in an electronic, optoelectronic, or nonlinear optical device. The compositions described herein can also be used in field effect transistors (FETs), thin-film transistors (TFTs), organic light-emitting diodes (OLEDs), PLED applications, electro-optic (EO) applications, as conductive materials, as two photon mixing materials, as organic semiconductors, as non-linear optical (NLO) materials, as RFID tags, as electroluminescent devices in flat panel displays, in photovoltaic devices, and as chemical or biological sensors. Compounds embodied herein may be used in devices described in U.S. Prov. Appl. No. 61/567,342, herein incorporated by reference in its entirety.

In some aspects, the fused thiophene-based polymers embodied herein have unexpectedly high hole mobilities, on/off ratios, or threshold voltages when incorporated into thin-film devices. In some embodiments, the hole mobilities of the fused thiophene-based polymers embodied herein are greater than 0.5 cm$^2$/V·s, 0.75 cm$^2$/V·s, 1.0 cm$^2$/V·s, 1.25 cm$^2$/V·s, 1.5 cm$^2$/V·s, 1.75 cm$^2$/V·s, 2.0 cm$^2$/V·s, 2.25 cm$^2$/V·s, 2.5 cm$^2$/V·s, 2.75 cm$^2$/V·s, 3.0 cm$^2$/V·s, 3.25 cm$^2$/V·s, 3.5 cm$^2$/V·s, 3.75 cm$^2$/V·s, or 4.0 cm$^2$/V·s. In some embodiments, the fused thiophene-based polymers embodied herein have an on/off ratio of greater than $10^5$, $10^6$, $10^7$, $10^8$, $10^9$, or $10^{10}$. In some embodiments, the fused thiophene-based polymers embodied herein have a threshold voltage less than 0.25 V, 0.5 V, 0.75 V, 1.0 V, 1.25 V, 1.5 V, 1.75 V, 2.0 V, 2.25 V, 2.5 V, 2.75 V, 3.0 V, 3.25 V, 3.5 V, 3.75, or 4.0 V.

The polymers comprising the fused thiophene moieties described herein (3, 3', 3", 4, 4', 4", 44', 45', 100, and 101) possess enhanced packing ability and thermal stability. The polymers also display liquid crystalline phases over certain temperature ranges. The liquid crystalline properties can easily be tuned by changing the length of the alkyl groups $R_1$ and $R_2$. The polymers also have good solubility in organic solvents such as, for example, THF, toluene, chlorobenzene, which permits the casting of thin films using techniques known in the art.

Described herein are methods for making fused thiophene compounds. In one aspect, the method for making a β"-R-substituted fused thiophene moiety comprises the steps of:

(i) providing an α-hydro β-bromo thiophene moiety;

(ii) converting the α-hydro β-bromo thiophene moiety to an α-(R-acyl)-β-carboxymethylthio thiophene moiety by acylating the thiophene moiety at the α-position with an R-acyl moiety, where R is an alkyl group having at least four carbons, (iii) substituting the β-bromide with a 2-mercaptoacetate;

(iv) cyclizing the α-(R-acyl)-β-carboxymethylthio thiophene moiety to form an α"-carboxy-β"-R-substituted fused thiophene moiety; and (v) decarboxylating the α"-carboxy β"-R-substituted fused thiophene moiety to form the β"-R-substituted fused thiophene moiety.

In one aspect, a method for making a β"-R-substituted fused thiophene compound is shown in the reaction scheme of FIG. 1. First, an α-hydro-β-bromo thiophene moiety 11 is provided. The α-hydro-β-bromo thiophene moiety 11 can be a simple unfused thiophene, as shown in structures 12 and 13 below. Structure 12 is an unsubstituted unfused α-hydro-β-bromo thiophene, which upon ring fusion produce thienothiophene 14 having a single 0 substitution. Structure 13 is R' substituted at the β' center (i.e., a α-hydro-β-bromo-β'-R'-substituted thiophene), which upon ring fusion produces a doubly β-substituted thienothiopene 15.

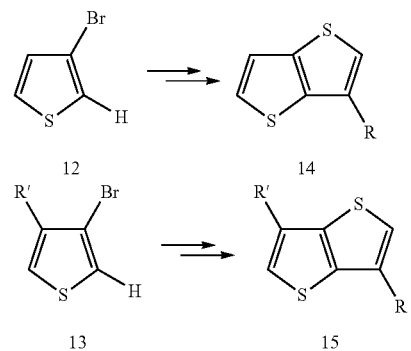

The α-hydro-β-bromo thiophene moiety is then converted to an α-(R-acyl)-β-carboxymethylthio thiophene moiety 16. As used herein, the name "R-acyl" is meant to denote radical structure 17 below, and the name "carboxymethylthio" is meant to denote radical structure 18 below, where Z is the terminus of the carboxylate (which may be, e.g., H, substituted alkyl, unsubstituted alkyl). In some embodiments, Z is H, methyl, ethyl or propyl. The reaction scheme shown in FIG. 2 and described in more detail in the examples can be used to effect the conversion of the α-hydro-β-bromo thiophene moiety 11 to the α-(R-acyl)-β-carboxymethylthio thiophene moiety 16. The α-hydro-β-bromo thiophene moiety is first acylated at the α-position with a R-acyl moiety using RCOCl and AlCl$_3$, where R is an alkyl group having at least four carbons. The acylated product is reacted with the 2-mercaptoacetate HSCH$_2$COOZ to yield the α-(R-acyl)-β-carboxymethylthio thiophene moiety 16. While in the reaction scheme of FIG. 2, the R-acylation is performed first, in certain cases the reactions can be performed in the opposite order.

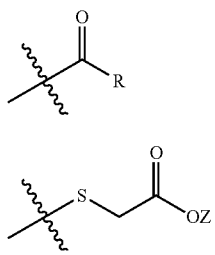

The α-(R-acyl)-β-carboxymethylthio thiophene moiety 16 is then cyclized (e.g., via a base-catalyzed condensation, often under the same conditions as the reaction with the 2-mercaptoacetate) to yield an α"-carboxy-β"-R-substituted fused thiophene moiety 19, which is decarboxylated to form the β"-R-substituted fused thiophene moiety 20, where R is an alkyl group having at least four carbons.

Figure 2:
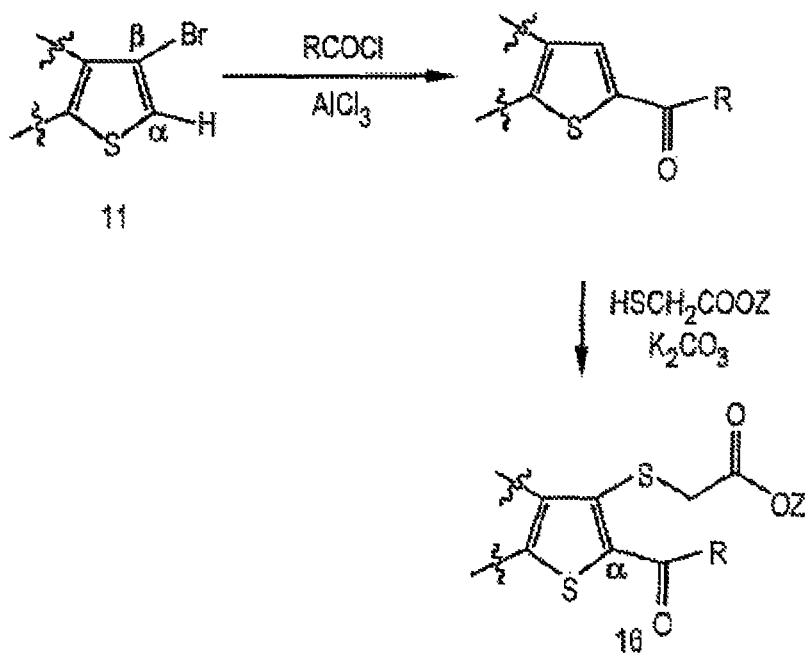
FIG. 2 is a reaction scheme showing a method for making an α-(R-acyl)-β-carboxymethylthio thiophene moiety.

If the α-hydro-β-bromo thiophene moiety 11 of the reaction scheme of FIG. 2 has a hydrogen at its α'-position, then the acylation step may not be specific to the α-position. For example, as shown in the reaction scheme of FIG. 3, α,α'-dihydro-β-bromo thiophene moiety 21 is acylated and reacted with a 2-mercaptoacetate, forming a mixture of products including the desired α-(R-acyl)-α'-hydro-β-carboxymethylthio thiophene moiety 22, as well as the undesired regioisomeric α'-hydro-α-(R-acyl)-β-carboxymethylthio thiophene moiety 23. Since moieties 22 and 23 are likely to be separable from one another, the cyclization step on the mixture can be performed; regioisomer 22 will cyclize to form α'-hydro-α"-carboxy-β"-R-substituted fused thiophene moiety 24, while regioisomer 23 will not cyclize. The fused thiophene moiety 24 can now be separated from uncyclized regioisomer 23, and can be decarboxylated to yield α'-hydro-β"-R-substituted fused thiophene moiety 25.

Figure 3:
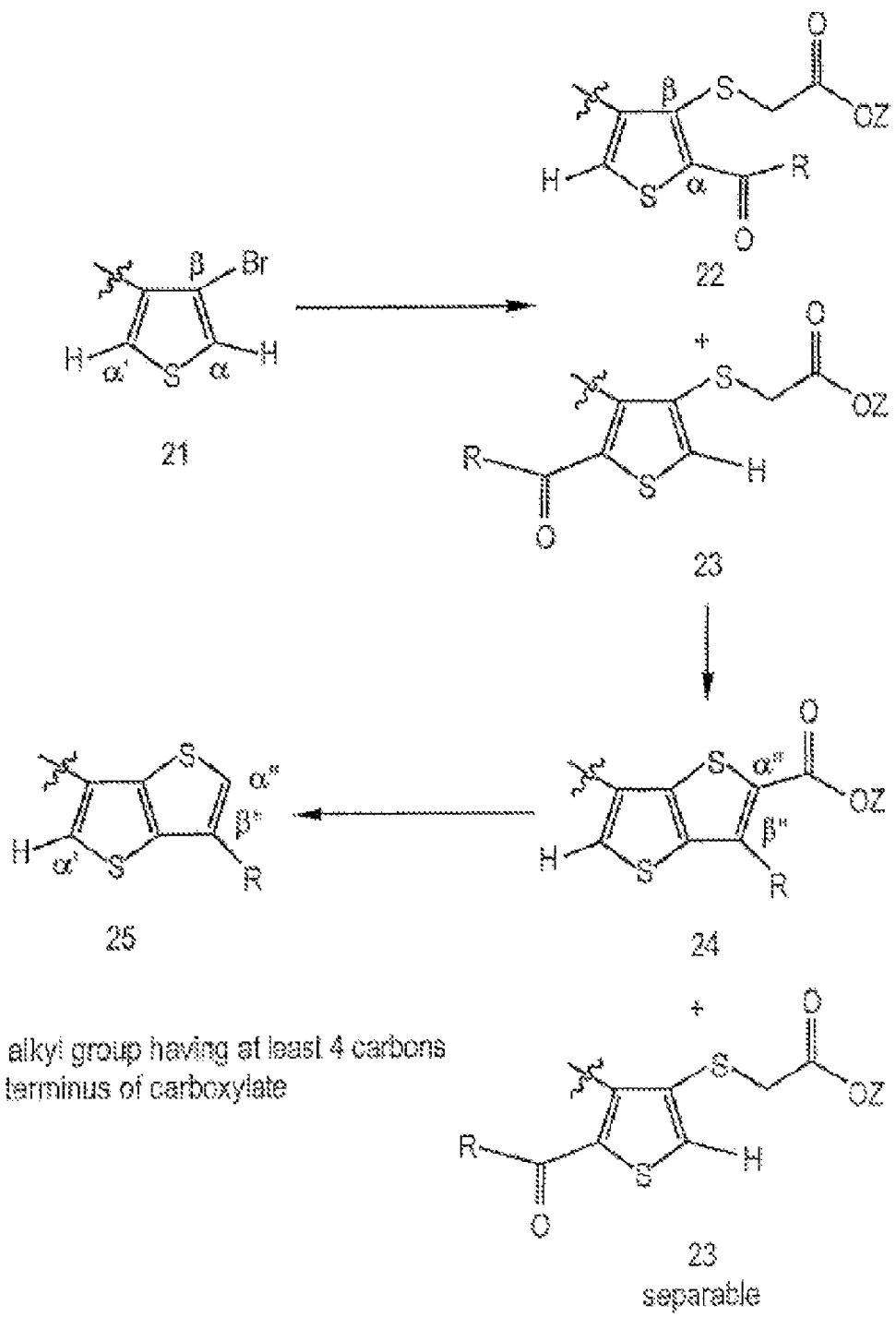
FIG. 3 is a reaction scheme showing a method for making an α'-hydro-β"-R-substituted fused thiophene moiety.

In other aspects, the methods described in the reaction schemes of FIGS. 2 and 3 can be used to make a variety of fused thiophene compounds. For example, if the α-hydro-β-bromo thiophene moiety 11 of the reaction scheme of FIG. 2 is an α-hydro-β-bromo-β'-R'-substituted thiophene moiety 13, then the end product fused thiophene will be a β"-R-substituted-β'-R'-substituted fused thiophene moiety 15. R' can be, for example, an alkyl group having at least four carbons, and can be the same as or different from R. R' can also be any other desired substitution, including an alkyl group having less than four carbons.

Figure 4:
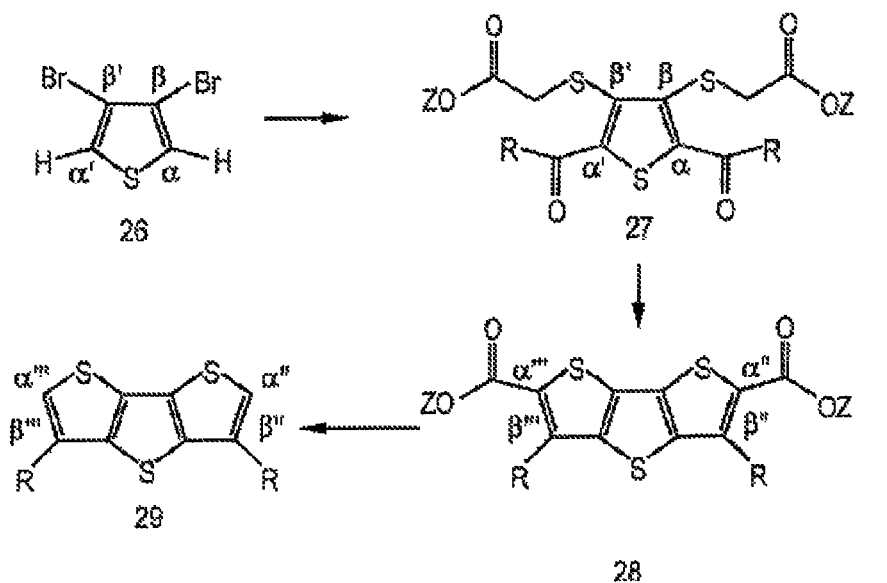
FIG. 4 is a reaction scheme in which there is a simultaneous cyclization on both sides of a thiophene moiety.

The general cyclization method of the reaction scheme of FIG. 2 can be used to simultaneously perform cyclization on both sides of a thiophene moiety, as shown in the reaction scheme of FIG. 4. An α,α'-dihydro-β,β'-dibromo thiophene moiety 26 is used as the starting material. While in the reaction scheme of FIG. 4 the α,α'-dihydro-β,β'-dibromo thiophene moiety 26 is shown as a monocyclic simple thiophene, the skilled artisan will understand that thiophene moiety 26 can have fused thiophenes (such as thieno[3,2-b]thiophene or bisdithieno[3,2-b:2'-3'-d]thiophene) as its fused thiophene ring system. Thiophene moiety 26 is acylated (for example, as described above using Friedel-Crafts chemistry) at both the α and α' positions, and is reacted with a 2-mercaptoacetate at both the β and β' positions to yield an α,α'-bis(R-acyl)-β,β'-bis(carboxymethylthio)thiophene moiety 27, which is cyclized (forming 28) and decarboxylated to form β",β'''-bis(R-substituted) fused thiophene moiety 29, which has a fused thiophene ring system that is two rings larger than that of the starting material thiophene moiety 26.

Alternatively, the α,α'-dihydro-β,β'-dibromo thiophene moiety can be subjected to a first series of R-acylation/reaction with 2-mercaptoacetate/cyclization/decarboxylation reactions, then to a second series of reactions with a different R' group in the acylation step to provide a β"-(R-substituted)-β'''-(R'-substituted) fused thiophene moiety in which R and R' are different from one another.

Figure 5:
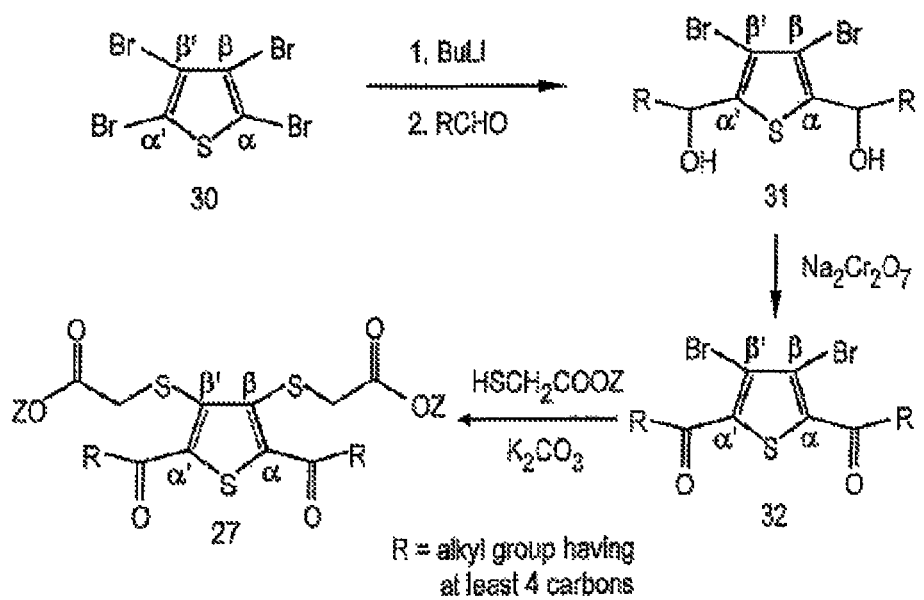
FIG. 5 is a reaction scheme showing an alternative method for making an α,α'-bis(R-acyl)-β,β'-bis(carboxymethylthio) thiophene moiety.

The reaction scheme of FIG. 5 shows an alternative way to make an α,α'-bis(R-acyl)-β,β'-bis(carboxymethylthio) thiophene moiety 27. An α,α',β,β'-tetrabromo thiophene moiety 30 is lithiated (selectively at the α-positions) and reacted with an aldehyde RCHO to form diol 31, which is oxidized to form α,α'-bis(R-acyl)-β,β'-dibromo thiophene moiety 32, which is reacted with a 2-mercaptoacetate to form the α,α'-bis(R-acyl)-β,β'-bis(carboxymethylthio)thiophene moiety 27.

Figure 6:
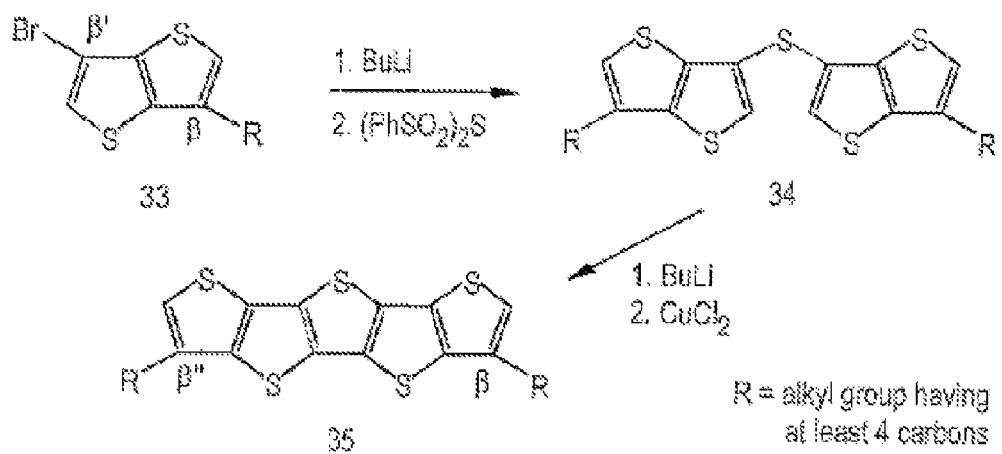
FIG. 6 is a reaction scheme showing a method for making a five-ring fused thiophene.

Fused thiophene moieties having relatively large fused thiophene ring systems can be synthesized using the reaction schemes described above. It is also possible to build large fused thiophene ring systems using the coupling and ring closure steps shown in the reaction scheme of FIG. 6. A β-R-substituted-β'-bromo thiophene moiety 33, in which R is an alkyl group, is used as the starting material in this scheme; synthetic routes to 33 are described below. While in the reaction scheme of FIG. 6, the β-R-substituted-β'-bromo thiophene moiety 33 is shown as having a thieno[3,2-b]thiophene ring system, it may also have a monocyclic thiophene, or a larger fused thiophene ring system as described above at its core. The β-R-substituted-β'-bromo thiophene moiety 33 is lithiated and reacted with sulfur bis(phenylsulfonate) (or sulfur dichloride) to form coupled thioether 34, which is lithiated and subjected to oxidative ring closure using $CuCl_2$ to form the β,β" disubstituted fused thiophene moiety 35.

Figure 7:
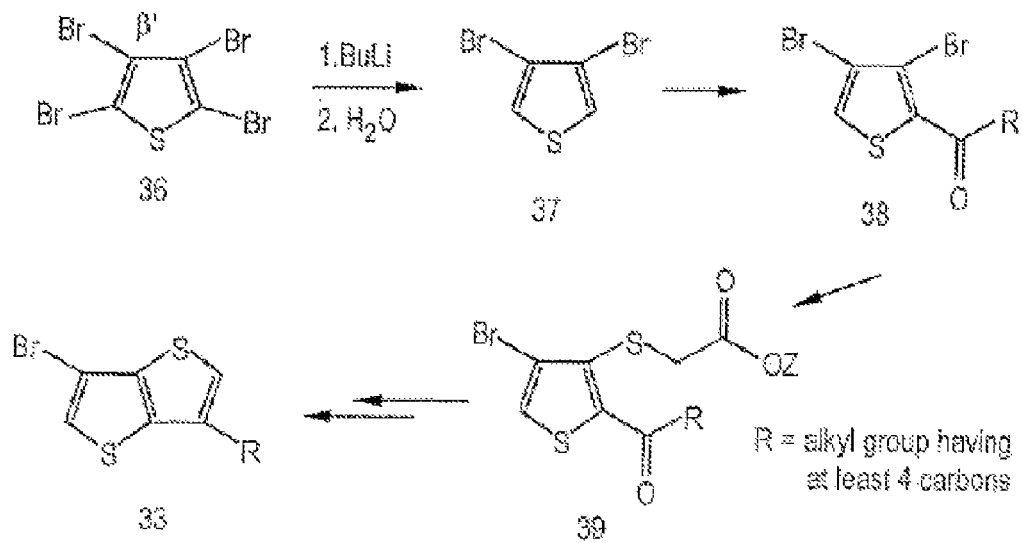
FIG. 7 is a reaction scheme showing a method for making polycyclic β-R-substituted-β'-bromo thiophene moieties.

Polycyclic β-R-substituted-β'-bromo thiophene moieties can be made by performing the reaction series of FIG. 2 on a β'-bromo thiophene moiety, as shown in the reaction scheme of FIG. 7. Tetrabromothiophene is dilithiated (selectively at the α-positions) and protonated to yield dibromothiophene 37, which is acylated (giving 38) and reacted with a 2-mercaptoacetate to give α-(R-acyl)-β-carboxymethylthio-β'-bromo thiophene moiety 39, which is cyclized and decarboxylated to yield 33. While the starting material in the reaction scheme of FIG. 7 is a monocyclic thiophene, polycyclic fused thiophene starting materials can be used as well.

In another aspect, described herein are β-R-substituted-β'-bromo thiophene compounds, in which R is an alkyl group as defined herein. For example, compounds described herein include those having structure 40, below. R can be, for example, an unsubstituted alkyl group.

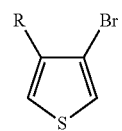

The unsubstituted alkyl group according to this aspect can be a straight-chain alkyl group (e.g. butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In one aspect, R can be an alkyl group at least seven, at least eight, at least nine, or at least ten carbons in size, which is substituted or unsubstituted.

In one aspect, the substitution of the alkyl group is separated from the fused thiophene ring system by at least two carbons. Examples of substituted alkyl groups according to this aspect include 6-hydroxyhexyl and 3-phenylbutyl. The selection of $R_1$ and $R_2$ moieties depends upon the end use of the fused thiophene moiety-containing composition. Any functionality on the substituted alkyl group can be protected in order to survive subsequent reaction steps. Unsubstituted thiophene-based compositions tend to be relatively insoluble; as such, in one aspect, R can be an alkyl group having at least six carbons in size. For example, alkyl groups for improving solubility include $C_kH_{2k+1}$, where k is an integer greater than or equal to six.

Figure 8:
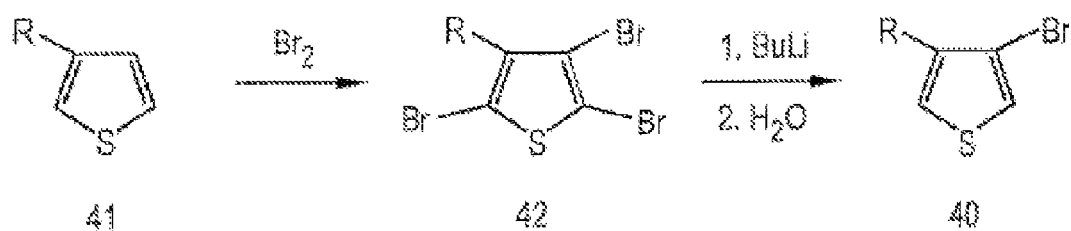
FIG. 8 is a reaction scheme showing a method for making β-R-substituted-β'-bromo thiophene compounds.
Figure 9:
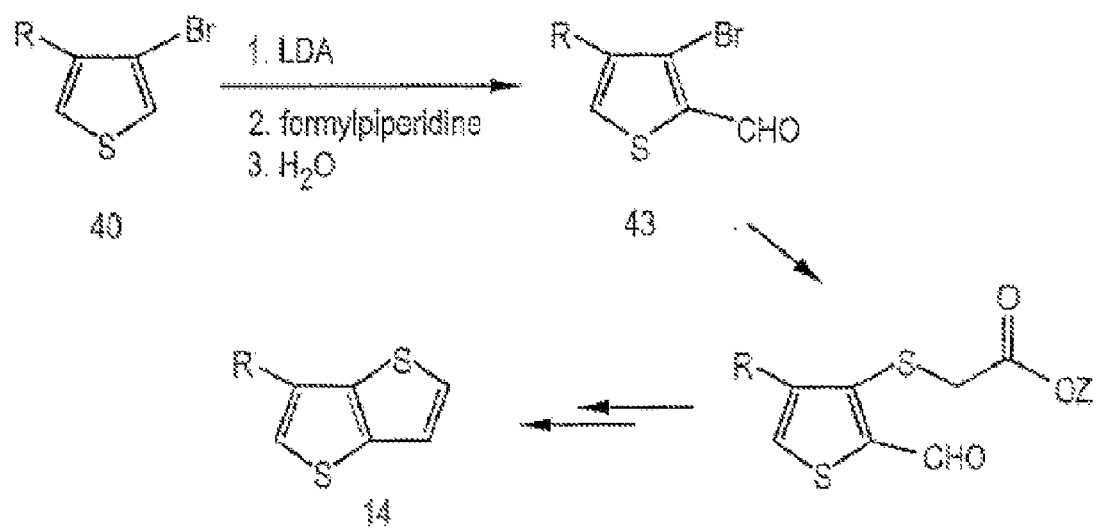
FIG. 9 is reaction scheme showing a method for making monosubstituted fused thiophene moieties.

In one aspect, compounds having structure 40 above can be synthesized from β-R-substituted thiophene moieties by the bromination/debromination method shown in FIG. 8. β-R-substituted thiophene 41 is fully brominated with molecular bromine to yield the tribrominated compound 42, which is selectively lithiated and protonated at the α-positions to yield the desired β-R-substituted-β'-bromo thiophene 40. The method of FIG. 8 can also be used to make β-brominated fused thiophene moieties from fused thiophene moieties. The monocyclic β-R-substituted-β'-bromo thiophene 40 can be used to make tricyclic bis(R-substituted) fused thiophene moieties according to the reaction scheme shown in FIG. 6. The monocyclic β-R-substituted-β'-bromo thiophene 40 can also be used to make monosubstituted fused thiophene moieties according to the reaction scheme shown in FIG. 9. For example, monocyclic thiophene 40 is lithiated and reacted with formylpiperidine, and the adduct is hydrolyzed to yield aldehyde 43, which is reacted with a 2-mercaptoacetate, cyclized and decarboxylated to yield β-R-substituted fused thiophene 14.

The oxidized fused thiophene compounds and moieties described herein, for example 44 and 45, can be prepared by oxidation of the prepared fused thiophene compounds, for example, with MCPBA. Oxidation is generally selective at the central-most rings of the polycyclic fused thiophene ring systems; however, it is contemplated that any of the sulfur atoms in the fused thiophenes can be oxidized.

Figure 18:
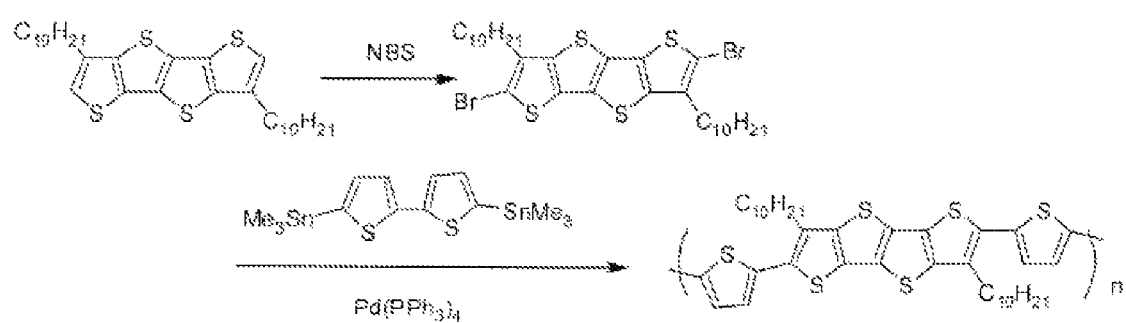
FIG. 18 is a reaction scheme for producing fused thiophene copolymers.
Figure 19A:
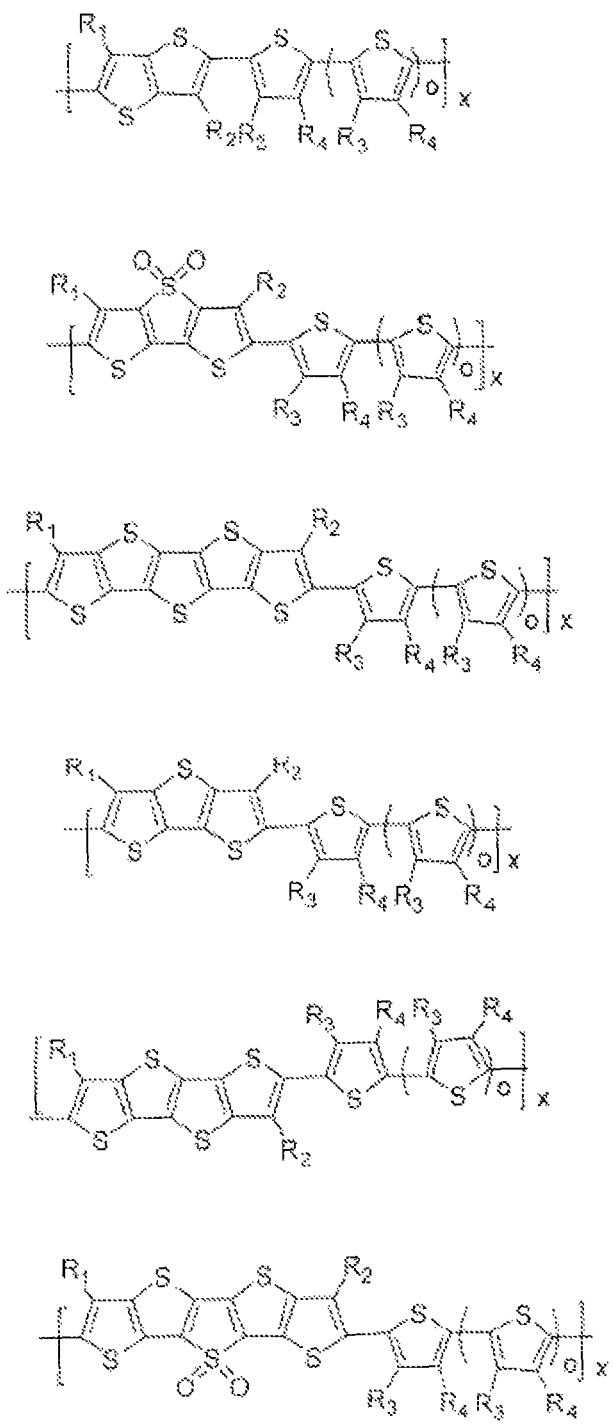
FIG. 19A and FIG. 19B show structures of different fused thiophene copolymers produced by the methods described herein.
Figure 19B:
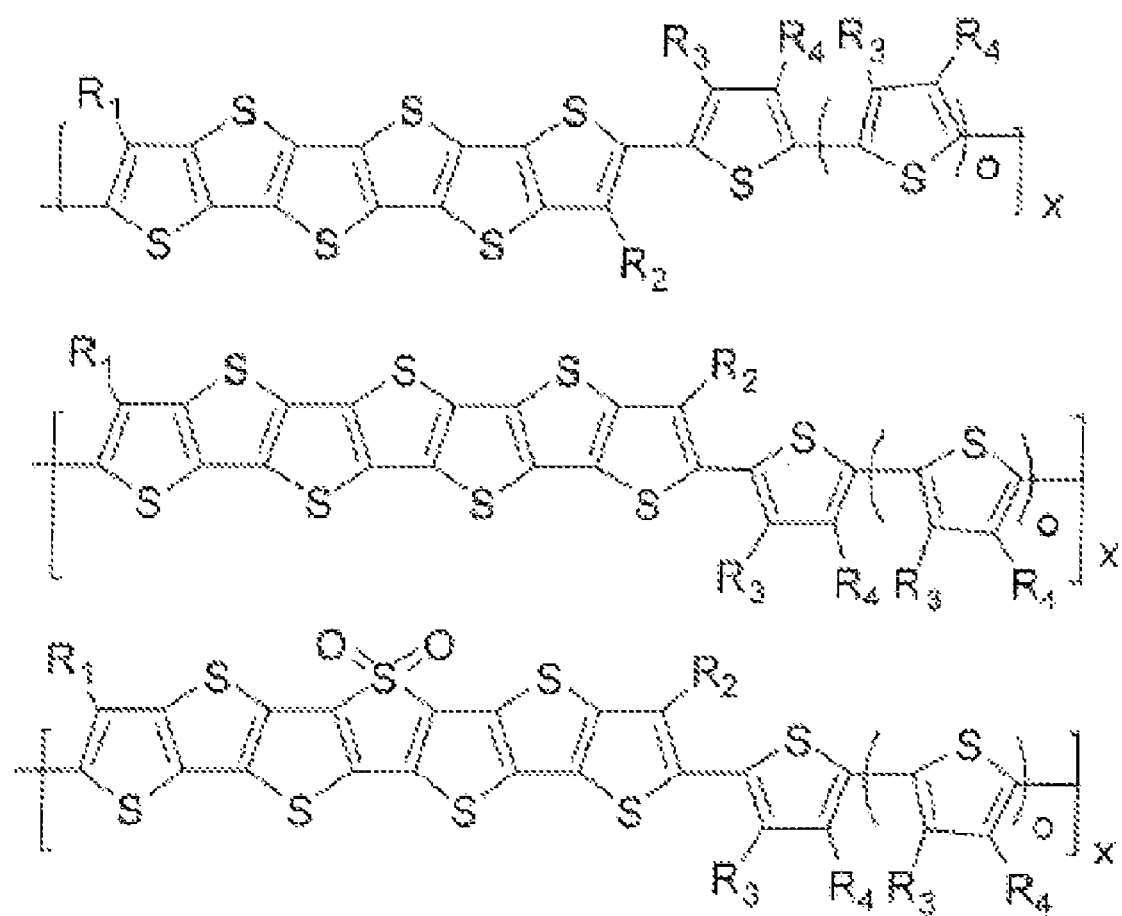

In one aspect, compounds comprising the moiety 3' or 4' can be produced by reacting a compound comprising the formula 210 or 220:

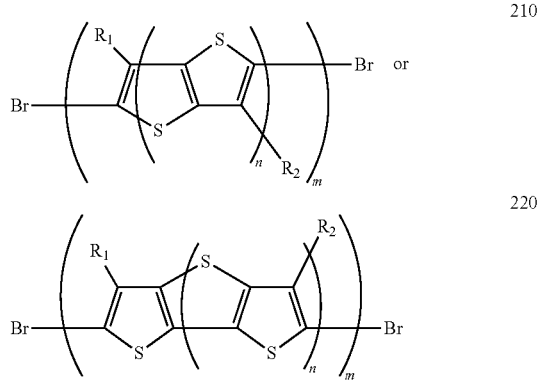

wherein n is an integer greater than or equal to one; in some embodiments, n is an integer of two or more; m is an integer greater than or equal to one; $R_1$ and $R_2$ are, independently, hydrogen or an alkyl group, wherein at least one of $R_1$ and $R_2$ is an alkyl group, with a compound having the formula $(R^5)_3Sn—Ar—Sn(R^5)_3$, wherein Ar comprises an aryl group and $R^5$ is an alkyl group. In this aspect, the dibromo-fused thiophene is coupled with a bis-stannyl aryl group. The coupling reaction is generally performed in the presence of a catalysts such as, for example Pd(0). FIG. 18 depicts one aspect of this method, where the dibromo-fused thiophene (formula 210, n=3, m=1) is coupled with 2,5'-distannyltrimethyl-bithiophene in the presence of $Pd(PPh_3)_4$ to produce a copolymer. Using this methodology, it is possible to produce co-polymers such as block co-polymers, where the value of m and o in 3' and 4' can vary depending upon the desired molecular weight of the copolymer.

Figure 20:
FIG. 20 shows a reaction scheme for forming the bis-tin-substituted FT4 from dibromo-FT4 by sequential reaction with butyllithium and trimethyltinchloride.

In another aspect, compounds comprising the moiety 3" or 4" can be produced through a series of synthetic steps. The fused thiophene core may be synthesized and brominated as described herein. The dibromo-fused thiophene may then be sequentially reacted with butyllithium and trimethyltinchloride to form the bis-tin-substituted fused thiophene as shown in FIG. 20. The formation of the dipyrrolopyrole moiety can be done via the reaction scheme shown in Tieke et al., Beilstein, J. ORG. CHEM. 830 (2010), herein incorporated by reference in its entirety, and is described in FIG. 21 for example compound 3,6-bis(5-bromothiophen-2-yl)-2,5-diheptadecylpyrrolo[3,4-c]pyrrole-1,4(2H,5H)-dione. The fused thiophene moiety and the dipyrrolopyrrole moiety may be combined to form 3" or 4" via any standard coupling reaction. In some aspects, the fused thiophene moiety and the dipyrrolopyrrole moiety may be combined via a Stille-type coupling reaction as shown in FIG. 22. The reaction in FIG. 22 uses palladium(II) catalyst as it showed good reliability, but palladium(O=0) based catalysts such as tetrakistriphenylphosphine palladium(0) could also be used.

Figure 27:
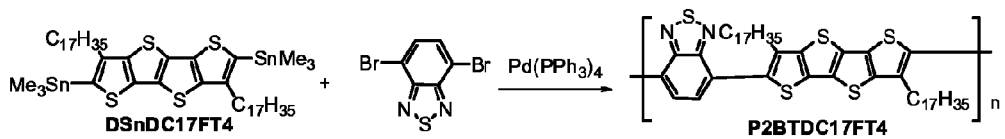
FIG. 27 describes the reaction scheme for forming a conjugated polymer comprising a FT4 coupled by a 4,7-benzo[c]-1,2,5-thiazole.

In another aspect, fused thiophene compounds comprising the moieties 300 or 301 can be produced through a series of synthetic steps. The fused thiophene core may be synthesized and brominated as described herein. The dibromo-fused thiophene may then be reacted with a palladium catalyst in a Stille-type reaction in the presence of tributylstannyl compound to give the aryl-containing polymers. Alternatively, the fused thiophene core may be reacted sequentially with butyllithium and trimethyltinchloride to form the bis-tin-substituted fused thiophene, which may be subsequently reacted with a brominated aryl moiety in a Stille-type reaction to form the conjugated polymer (FIG. 27). The reaction in FIG. 27 uses palladium(0) catalyst as it showed good reliability, but palladium(II) based catalysts such as may also be used.

Figure 25:
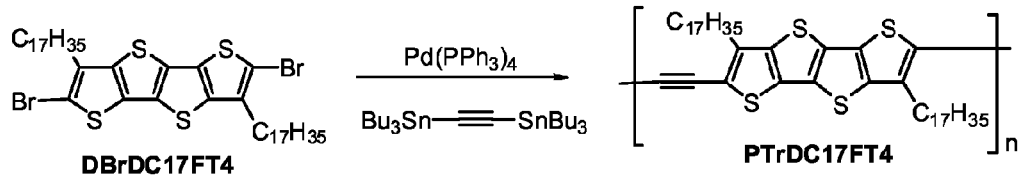
FIG. 25 describes the reaction scheme for forming a conjugated polymer comprising a FT4 coupled by a triple bond.
Figure 26:
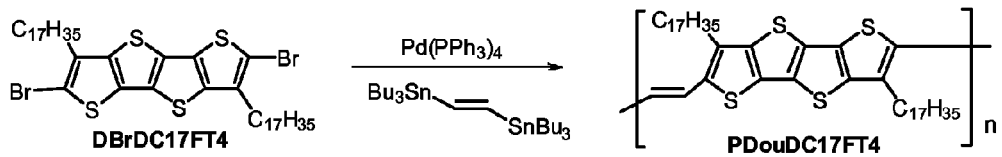
FIG. 26 describes the reaction scheme for forming a conjugated polymer comprising a FT4 coupled by a double bond.

In another aspect, compounds comprising the moieties 100 or 101 can be produced through a series of synthetic steps. The fused thiophene core may be synthesized and brominated as described herein. The dibromo-fused thiophene may then be reacted with a palladium catalyst in a Stille-type reaction in the presence of tributylstannyl compound to give the conjugated polymer (FIGS. 25 and 26). Alternatively, the fused thiophene core may be reacted sequentially with butyllithium and trimethyltinchloride to form the bis-tin-substituted fused thiophene, which may be subsequently reacted with a brominated moiety in a Stille-type reaction to form the conjugated polymer. (FIGS. 25 and 26). The reaction in FIGS. 25 and 26 uses palladium(0) catalyst as it showed good reliability, but palladium(II) based catalysts such as could also be used.

Fused thiophene and oxidized fused thiophene oligomers and polymers can be prepared using methodologies similar to those used in making oligo- and poly(thiophenes) described above. For example, α,α'-dihydro fused thiophene moieties can be oxidatively oligomerized or polymerized using iron (III) compounds (e.g., $FeCl_3$, $Fe(acac)_3$), or can be brominated and coupled in an organomagnesium mediated reaction. The fused thiophene moieties and oxidized fused thiophene moieties described herein can be incorporated into other conjugated polymers such as, for example phenylene, vinylene, and acetylene copolymers, using coupling reactions familiar to the skilled artisan. The fused thiophene moieties and oxidized fused thiophene moieties described herein can be incorporated into other main chain and side chain polymers using techniques known in the art. It is contemplated that the fused thiophene compound can be oxidized prior to incorporation into an oligomer or polymer. In the alternative, the fused thiophene compound can be incorporated into the oligomer or polymer followed by oxidation.

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of the description. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Figure 10:
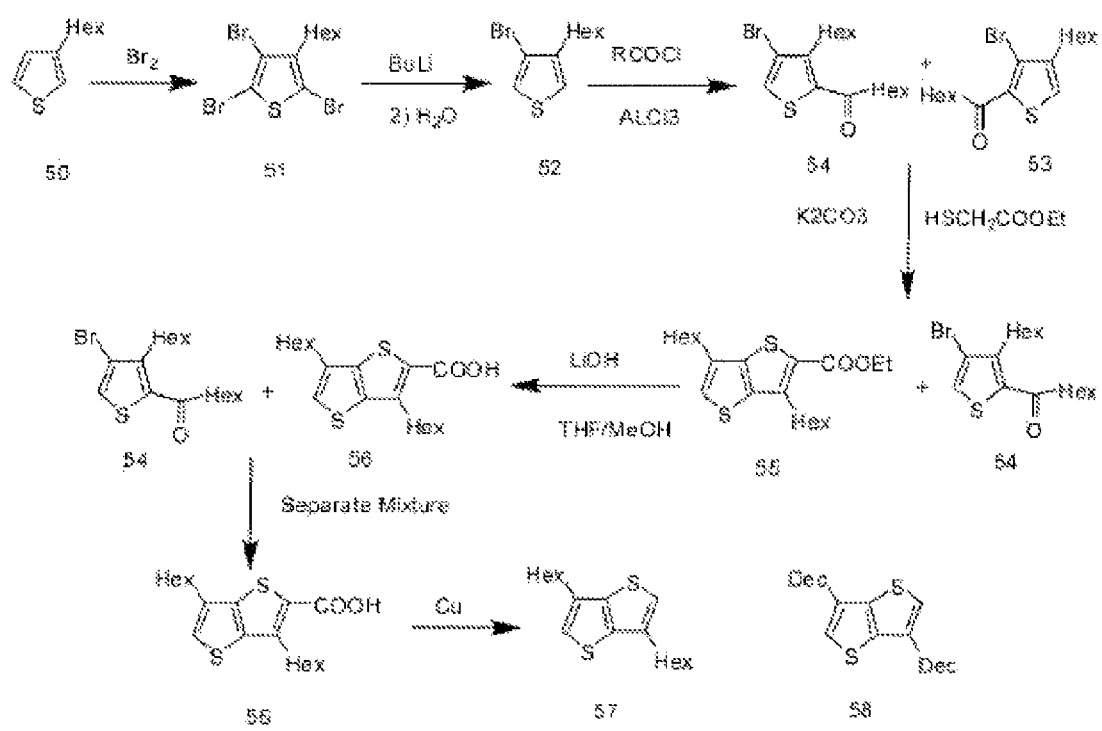
FIG. 10 is a reaction scheme showing the synthesis of 3,6-dihexylthieno[3,2-b]thiophene and 3,6-didecylthieno[3,2-b]thiophene according to Example 1.

Di-(3-substituted thieno[3,2-b]thiophenes 3,6-dihexylthieno[3,2-b]thiophene 57 is synthesized as shown in the reaction scheme of FIG. 10.

2,4,5-Tribromo-3-hexylthiophene (51)

3-Hexylthiophene (50) (100 g, 0.595 mol) is mixed with 200 mL acetic acid. To this mixture, bromine (88 mL, 1.33 mol) is added dropwise. After addition of the bromine, the resulting mixture is stirred at room temperature for 4 hours, heated to 60-70° C. overnight, then poured into 800 mL ice water and neutralized with 6M aqueous NaOH. The mixture is extracted with ethyl acetate (3×100 mL). The combined organic layers are washed with brine (2×100 mL) and water (100 mL) and dried over $MgSO_4$. Evaporation of the solvent yielded crude 51 (234 g, 97.1% crude yield). This crude product is sufficiently pure for use in subsequent reactions. GC/MS: 404 g/mol (M−1). $^1$H NMR ($CD_2Cl_2$): δ 2.64 (t, 2H), 1.51 (m, 2H), 1.32 (m, 6H), 0.89 (t, 3H). $^{13}$C NMR: 143.69, 117.86, 111.48, 110.18, 33.62, 32.86, 30.96, 30.52, 24.70, 16.00.

3-Bromo-4-hexylthiophene (52)

Compound 51 (70 g, 0.173 mol) is mixed with dry THF (400 mL). To this mixture, n-butyllithium (138 mL, 2.5M in hexane, 0.345 mol) is added dropwise at −78° C. under argon. The resulting mixture is stirred for 10 minutes, then water (30 mL) is added to quench the reaction. The THF is evaporated and the organic is extracted with ethyl acetate (2×100 mL). The combined organic layers are washed with brine (2×100 mL), water (70 mL) and dried over $MgSO_4$. After evaporation of the solvent, the resulting crude product is purified by vacuum distillation (72-74° C. at 0.17 mbar) to yield 52 (35.3 g, 82.6% yield). GC/MS: 246 g/mol (M−1). $^1$H NMR ($CD_2Cl_2$): δ 7.22 (s, 1H), 6.96 (s, 1H), 2.57 (t, 2H), 1.61 (m, 2H), 1.32 (m, 6H), 0.88 (t, 3H). $^{13}$C NMR: 141.92, 122.87, 120.95, 112.89, 31.88, 30.07, 29.53, 29.20, 22.88, 14.14.

1-(3-Bromo-4-hexyl-2-thienyl)heptanone (53)

Heptanoyl chloride (14.9 g, 0.1 mol) is added dropwise at room temperature to a mixture of compound 52 (24.7 g, 0.1 mol) and $AlCl_3$ (26.8 g, 0.2 mol) in dry $CH_2Cl_2$ (100 mL). This mixture is stirred for approximately two hours, or until which time GC/MS analysis indicates that a 3:1 mixture of target compound 53 and its regioisomer 1-(4-bromo-3-hexyl-2-thienyl)heptanone (54) has been formed. The reaction mixture is poured into 200 mL 6 M HCl and washed with water (3×50 mL). The organic layer is then dried over $MgSO_4$. Evaporation of the solvent yields 34.7 g of a crude mixture of compounds 53 and 54, which is used without separation or further purification in the next reaction.

3,6-Dihexylthieno[3,2-b]thiophene-2-carboxylic acid (55)

The mixture of compounds 53 and 54 (66.5 grams, 0.185 mol) is mixed with $K_2CO_3$ (53.6 grams, 0.39 mol) and a catalytic amount of 18-crown-6 in 200 mL DMF. To this mixture, ethyl 2-mercaptoacetate (20.3 mL, 0.185 mol) is added dropwise at 60-70° C. The reaction mixture is stirred at 60-70° C. overnight, then poured into water (800 mL). The organic component is extracted with ethyl acetate (3×100 mL) and the combined organic extracts are washed with brine (2×100 mL) and water (100 mL). The solvent is removed by evaporation, and the residue is dissolved in THF (300 mL), forming a solution to which LiOH (84 mL, 10% solution in water), MeOH (50 mL) and a catalytic amount of tetrabutylammonium iodide are added. The mixture is heated at reflux for 3 hours, after which time the solvent is removed by evaporation, and the residue acidified with concentrated HCl (50 mL). After dilution with 200 mL water, the organic component is extracted with ethyl acetate (3×100 mL). The combined organic layers are washed with brine (2×100 mL), water (100 mL) and dried over $MgSO_4$. After evaporation of the solvent, the compound 55 is separated from unreacted compound 54 using column chromatography ($SiO_2$/5% ethyl acetate in hexane with 20% ethyl acetate in hexane to fully elute the compound 55), providing pure compound 55 (30 g, 46.1% yield). $^1$H NMR ($CD_2Cl_2$): δ 7.24 (s, 1H), 3.18 (t, 2H), 2.73 (t, 2H), 1.75 (m, 4H), 1.34 (m, 14H), 0.89 (m, 6H). $^{13}$C NMR: 169.15, 146.25, 143.10, 141.49, 136.14, 126.67, 126.11, 31.99, 29.74 (6C), 22.99, 14.24.

3,6-Dihexylthieno[3,2-b]thiophene (57)

A mixture of compound 55 (30 g, 0.085 mol), copper powder (3.76 g) and quinoline (80 mL) is heated at 264-260° C. in a Woods metal bath. When no further bubbles of carbon dioxide gas are detected (about 2 hours), the mixture is allowed to cool to room temperature and hexane (200 mL) is added. This mixture is washed repeatedly with HCl (1-2 M in water) to remove the quinoline. The remaining organic layer is dried over $MgSO_4$ and concentrated by evaporation, leaving a residue, which is purified by column chromatography ($SiO_2$/hexanes) to yield compound 57 (18 g, 68.4%). m.p. 57.5-59.1° C., $^1$H NMR ($CD_2Cl_2$): δ 6.97 (s, 2H), 2.70 (t, 4H), 1.73 (m, 4H), 1.37 (m, 12H), 0.88 (t, 6H). $^{13}$C NMR: 136.56, 134.96, 109.80, 31.94, 29.31, 29.28, 28.47, 22.96, 14.22.

The same reaction sequence is used to make 3,6-didecylthieno[3,2-b]thiophene (58).

Example 2

Mono-β-substituted thieno[3,2-b]thiophenes

Figure 11:
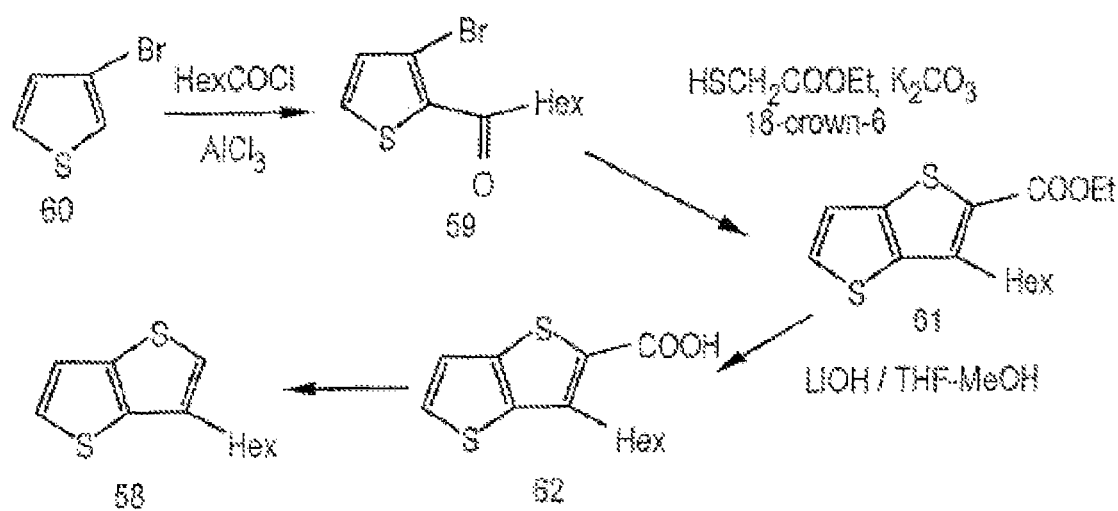
FIG. 11 is a reaction scheme showing the synthesis of 3-hexylthieno[3,2-b]thiophene according to Example 2.

3-Hexylthieno[3,2-b]thiophene 58 is synthesized as shown in the reaction scheme of FIG. 11.

1-(3-Bromothienyl)heptanone (59)

Heptanoyl chloride (14.9 g, 0.1 mol) is added dropwise at room temperature to a mixture of 3-bromothiophene (60) (16.3 g, 0.1 mol), AlCl$_3$ (26.8 g, 0.2 mol) and CH$_2$Cl$_2$ (100 mL). The resulting mixture is stirred for approximately two hours, or until which time GC/MS analysis indicates complete conversion of compound 60 to compound 59. The reaction mixture is poured into cold HCl (6M, 200 mL). The organic component is extracted with hexane (3×100 mL). The combined organic layers are washed with brine (2×100 mL) and water (100 mL). After drying over MgSO$_4$, the crude target compound is purified by column chromatography (SiO$_2$/hexanes) to yield compound 59 (25.1 g, 91.3% yield). GC/MS: 275 g/mol (M) $^1$H NMR (CD$_2$Cl$_2$): δ 7.53 (d, 1H), 7.12 (d, 1H), 3.01 (t, 2H), 1.71 (m, 2H), 1.38 (m, 6H), 0.92 (t, 3H).

Ethyl 3-hexylthieno[3,2-b]thiophene-2-carboxylate (61)

Compound 59 (35.4 g, 0.13 mol) and K$_2$CO$_3$ (27.6 g, 0.2 mol) are mixed with N,N-dimethylformamide (100 mL). A catalytic amount (~25 mg) 18-crown-6 is added, and to this mixture, ethyl 2-mercaptoacetate (14.0 mL, 0.13 mol) is added dropwise at 60° C. The mixture is stirred overnight and poured into water (500 mL). The organic component is extracted with ethyl acetate (3×80 mL). The combined organic layers are washed with brine (2×100 mL) and water (100 mL). The organic layer is then dried over MgSO$_4$. After evaporation of the solvent, the crude compound 61 is obtained and purified by column chromatography (SiO$_2$/5% ethyl acetate in hexanes) to yield pure compound 61 (32.1 g, 84.5%). GC/MS: 296 g/mol (M). $^1$H NMR (CD$_2$Cl$_2$): δ 7.56 (d, 1H), 7.24 (d, 1H), 4.34 (q, 2H), 3.15 (t, 2H), 1.71 (m, 2H), 1.32 (m, 6H), 0.88 (m, 6H). $^{13}$C NMR: 163.24, 143.31, 141.85, 141.09, 131.13, 128.44, 120.35, 61.25, 31.99, 29.72 (overlap), 22.98, 14.52, 14.23.

3-Hexylthieno[3,2-b]thiophene-2-carboxylic acid (62)

Compound 61 (32.1 g, 0.11 mol) is mixed with LiOH (10% in water, 50 mL), THF (100 mL), MeOH (30 mL) and a catalytic amount (~20 mg) tetrabutylammonium iodide in a 500 mL flask. This mixture is heated at reflux overnight, allowed to cool to room temperature, and acidified with concentrated HCl. The resultant yellow solid is collected by filtration and washed thoroughly with water. The solid then is heated with hexane (100 mL) allowed to cool to room temperature. After filtration, the solid is collected, dried over vacuum to yield compound 62 as a light yellow powder (28.0 g, 96.7% yield). M.P.: 110.7-112.4° C.

3-Hexylthieno[3,2-b]thiophene (58)

A mixture of compound 62 (14.6 g, 0.054 mol), copper powder (2.00 g), and quinoline (80 mL) is heated at about 260° C. in a Woods metal bath. When no further bubbles of CO$_2$ are detected (about 2 hours), the mixture is allowed to cool to room temperature, and hexane (200 mL) is added. The mixture is washed repeatedly with HCL (1-2 M in water) to remove the quinoline. The organic layer is dried over MgSO$_4$ and concentrated by evaporation. The residue is purified by column chromatography (SiO$_2$/hexanes) to yield compound 58 (25.1 g, 90.3% yield). GC/MS: 224 g/mol (M). $^1$H NMR (CD$_2$Cl$_2$): δ 7.36 (m, 1H), 7.25 (m, 1H), 7.01 (m, 1H), 2.73 (t, 2H), 1.69 (m, 2H), 1.34 (m, 6H), 0.89 (t, 3H). $^{13}$C NMR: 140.39, 139.13, 135.39, 127.01, 122.19, 120.26, 32.01, 30.29, 29.43, 23.01, 14.24.

Figure 12:
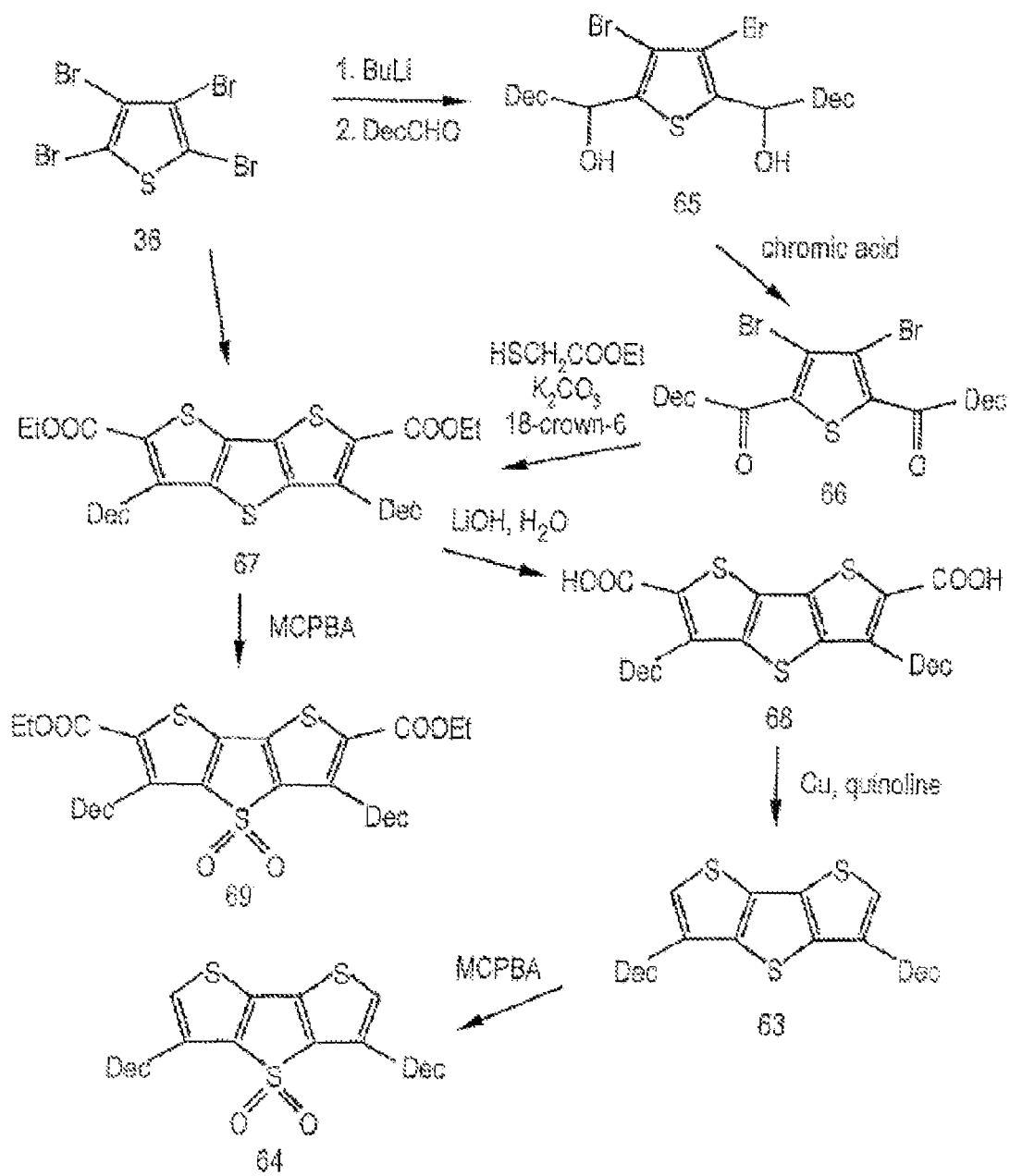
FIG. 12 is a reaction scheme showing the synthesis of 3,6-didecylthieno[3,2-b]thiophene and 3,6-didecylthieno[3,2-b]thiophene-4,4-dioxide according to Example 3.

Example 3 di-β-substituted dithieno[3,2-b:2'-3'-d]thiophenes and di-β-substituted dithieno[3,2-b:2'-3'-d] thiophene-4,4-dioxides 3,6-didecylthieno[3,2-b]thiophene 63 and 3,6-didecylthieno[3,2-b]thiophene-4,4-dioxide 64 are synthesized as shown in the reaction scheme of FIG. 12.

1,1'-(3,4-Bromo-2,5-thienyl)diundecanol (65)

Butyllithium (160 mL, 0.4 mol, 2.5M in hexanes) is added dropwise at −78° C. to a solution of tetrabromothiophene 36 (80.0 g, 0.2 mol) and THF (500 mL). Undecylic aldehyde (DecCHO) (69.7 g, 0.41 mol) is added, and the reaction mixture is stirred for two hours. The THF solvent is then removed by evaporation, and the organic residue is extracted with hexanes. The combined organic layers are washed by brine (2×100 mL) and water (100 mL) and dried over MgSO$_4$. The crude product is purified by column chromatography (SiO$_2$/5% ethyl acetate in hexanes) to yield compound 65 (84.1 grams, 72.5% yield). $^1$H NMR (CD$_2$Cl$_2$): δ 5.02 (broad, 2H), 1.79 (m 4H), 1.28 (m, 32H), 0.88 (t, 6H). $^{13}$C NMR: 143.25, 109.67, 70.53, 38.31, 31.96, 29.75, 29.70, 29.61, 29.55, 29.21, 25.68, 22.84, 14.09.

1,1'-(3,4-bromo-2,5-thienyl)diundecanone (66)

A chromic acid solution is prepared by dissolving 100 grams of sodium dichromate dihydrate (0.34 mol) is in water (300 mL), then 136 grams of concentrated sulfuric acid is added, and the resulting solution is diluted to 500 mL. Compound 65 (80.0 g, 0.137 mol) is mixed with acetone (300 mL), and to this mixture, the chromic acid solution (260 mL) is added dropwise at room temperature. The mixture is stirred overnight, after which time considerable solid had formed in the reaction mixture. Most of the acetone is decanted and the rest of the mixture is extracted with ethyl acetate (2×100 mL). The combined organic layers are washed with brine (3×50 mL) and dried over MgSO$_4$. The solvent is evaporated, and the residue is mixed with ethanol (100 mL) and white and pure compound 66 solidified and is collected by filtration (72.0 g, 90.5% yield). M.P.: 69.5-70.8° C. $^1$H NMR (CD$_2$Cl$_2$): δ 3.07 (t, 4H), 1.74 (m, 4H), 1.28 (m, 28H), 0.88 (t, 6H). $^{13}$C NMR: 192.49, 141.99, 118.82, 42.03, 32.13, 29.79, 29.71, 29.62, 29.55, 29.29, 24.16, 22.92, 14.11.

Diethyl 3,5-didecyldithieno[3,2-b:2',3'-d]thiophene-2,6-dicarboxylate (67)

Compound 66 (30.0 g, 0.052 mol) is mixed with K$_2$CO$_3$ (28.7 g, 0.21 mol) and N,N-dimethylformamide (100 mL). To this mixture, ethyl 2-mercaptoacetate (11.5 mL, 0.104 mol) is added dropwise at 60° C. The reaction mixture is stirred for 48 hours at 60° C. under nitrogen, then is poured into water (500 mL). The organic component is extracted with ethyl acetate (3×100 mL). The combined organic layers are washed with brine (2×100 mL) and water (50 mL) and dried over $MgSO_4$. The solvent is evaporated, and the residue is purified by column chromatography ($SiO_2$/5% ethyl acetate in hexanes) to give compound 67 as sticky, low melting point solid (19.1 g, 59.3% yield). $^1H$ NMR ($CD_2Cl_2$): δ 4.36 (q, 4H), 3.15 (t, 4H), 1.73 (m, 4H), 1.39 (m, 36H), 0.87 (m, 6H). $^{13}C$ NMR: 162.86, 145.47, 144.51, 133.05, 128.99, 61.63, 32.33, 29.99 (overlap), 23.11, 14.53, 14.31.

3,5-Didecanyldithieno[3,2-b:2',3'-d]thiophene-2,6-dicarboxylic acid (68)

Compound 67 (10.2 g, 0.017 mol) is mixed with LiOH (1.0 g in 10 mL water), THF (100 mL), MeOH (20 mL) and a catalytic amount (~35 mg) of tetrabutylammonium iodide. This mixture is heated at reflux overnight, then most of the solvent is evaporated. The residue is acidified with concentrated HCl (30 mL), forming a solid which is collected by filtration, washed thoroughly with water, and vacuum dried to yield compound 68 (8.6 g, 98% yield). M.P.: 280.1° C. $^1H$ NMR ($CD_2Cl_2$): δ 3.24 (t, 4H), 1.72 (m, 2H), 1.29 (m, 30H), 0.88 (t, 6H). $^{13}C$ NMR: 168.46, 148.24, 146.58, 136.32, 35.91, 33.64, 28.91 (m, overlap), 26.60, 17.49.

3,5-Didecyldithieno[3,2-b:2',3'-d]thiophene (63)

Compound 68 (8.6 g, 0.016 mol), copper powder (0.7 g) and quinoline (50 mL) are combined and heated at 250-260° C. in a Woods metal bath. When no further bubbles of carbon dioxide gas could be detected (about 2 hours), the mixture is cooled to room temperature and hexane (200 mL) is added. This mixture is washed repeatedly with HCl (1-2 M in water) to remove quinoline. The organic layer is dried over $MgSO_4$ and concentrated by evaporation, and the residue is purified by column chromatography ($SiO_2$/hexanes) to yield compound 63 (3.4 g, 47.4%). $^1H$ NMR ($CD_2Cl_2$): δ 6.97 (s, 2H), 2.73 (t, 4H), 1.78 (m, 4H), 1.27 (m, 28H), 0.88 (t, 6H). $^{13}C$ NMR: 141.89, 136.75, 130.99, 120.57, 32.33, 30.02, 29.79 (m, overlap), 29.74, 29.15, 23.10, 14.28.

Compounds 64 and 69 are prepared using the method described in Sogiu et al., 68 J. ORG. CHEM. 1512-1520 (2003), which is incorporated herein by reference.

3,5-Didecyldithieno[3,2-b:2',3'-d]thiophene-4,4-dioxide (64)

3-chloroperbenzoic acid (6.1 g, 0.035 mol), in 20 mL $CH_2Cl_2$ is added dropwise to a solution of 63 (3.64 g, 8.18 mmol) in 20 mL dichloromethane. The mixture is stirred at room temperature overnight, then washing sequentially with 10% KOH, 10% $NaHCO_3$ and brine. The organic layer is dried over $Mg_2SO_4$, and the solvent is removed by evaporation. The crude product is purified by column chromatography ($SiO_2$/5% ethyl acetate in hexanes) to give compound 64 as a yellow solid (1.4 g, 35.9% yield). M.p. 58.7-60.3° C. $^1H$ NMR ($CD_2Cl_2$) δ 6.94 (s, 2H), 2.73 (t, 4H), 1.72 (m, 4H), 1.27 (m, 28H), 0.88 (t, 6H). $^{13}C$ NMR: 142.99, 139.06, 136.36, 124.51, 32.27, 30.11, 29.95, 29.91, 29.68, 29.48, 29.51, 28.51, 23.04, 14.22.

Diethyl 3,5-didecyldithieno[3,2-b:2',3'-d]thiophene-4,4-dioxide-2,6-dicarboxylate (69). 3-chloroperbenzoic acid (1.2 g, 6.9 mmol), in 20 mL $CH_2Cl_2$ is added dropwise to a solution of 67 (3.64 g, 8.18 mmol) in 20 mL dichloromethane. The mixture is stirred at room temperature overnight, then washing sequentially with 10% KOH, 10% $NaHCO_3$ and brine. The organic layer is dried over $MgSO_4$, and the solvent is removed by evaporation. The crude product is purified by column chromatography ($SiO_2$/5% ethyl acetate in hexanes) to give compound 69 as a waxy solid (0.56 g, 53% yield). $^1H$ NMR ($CD_2Cl_2$) δ 4.39 (q, 4H), 3.13 (t, 4H), 1.72 (m, 4H), 1.27 (m, 34H), 0.88 (t, 6H). $^{13}C$ NMR: 161.41, 145.52, 144.77, 137.56, 132.89, 62.03, 32.11, 30.59, 29.82, 29.78, 29.75, 29.53, 29.49, 27.88, 22.89, 14.21, 14.07.

The reaction scheme of FIG. 12 is also used to make 3,5-dihexyldithieno[3,2-b:2',3'-d]thiophene and 3,5-dihexyldithieno[3,2-b:2',3'-d]thiophene-4,4-dioxide.

Figure 13:
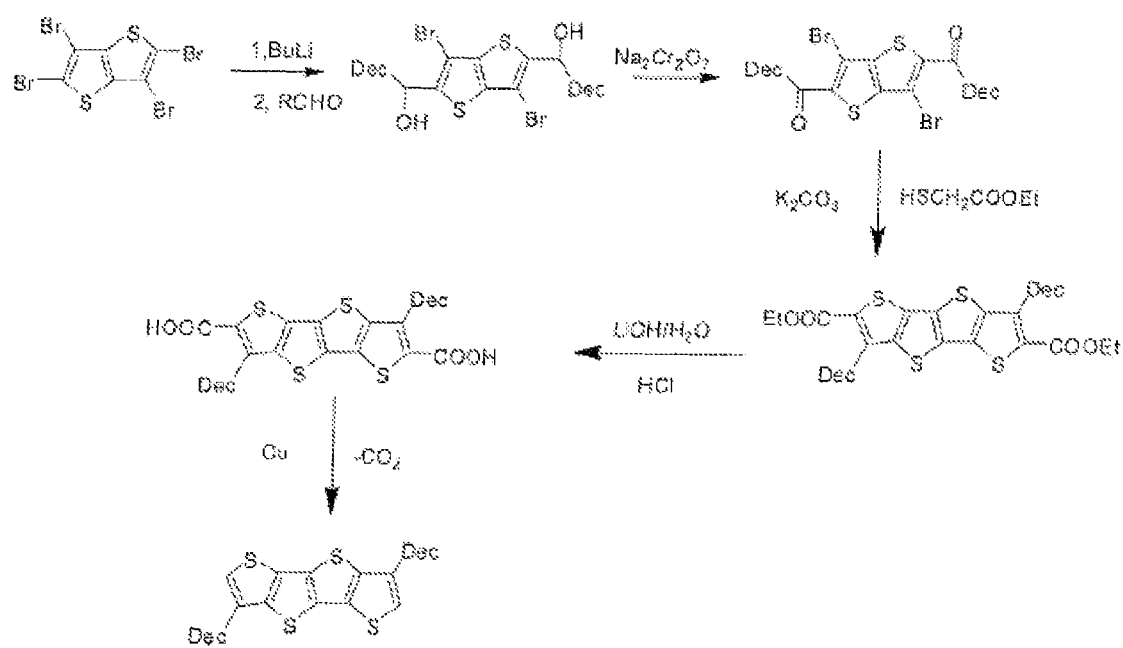
FIG. 13 is a reaction scheme showing the synthesis of 3,7-didecylthieno[3,2-b]thieno[2',3':4,5]thieno[2,3-d]thiophene according to Example 4.

Example 4 di-β-substituted thieno[3,2-b]thieno[2',3':4,5]thieno[2,3-d]thiophenes 3,7-Didecylthieno[3,2-b]thieno[2',3':4,5]thieno[2,3-d]thiophene 70 is synthesized as shown in the reaction scheme of FIG. 13.

2,4-di(1-hydroxydecyl)-3,6-dibromothieno[3,2-b]thiophene (72)

2,3,4,5-tetrabromothieno[3,2-b]thiophene (71) is prepared according to Fuller et al., 1 J. CHEM. SOC., PERKIN TRANS, 3465 (1997), which is hereby incorporated herein by reference. Butyllithium (70 mL, 0.175 mol, 2.5 M in hexanes) is added dropwise at −78° C. to a mixture of compound 71 (40.0 g, 0.088 mol) in 300 mL dry THF. The resulting mixture is stirred another 10 to 20 minutes and undecyl aldehyde (30.0 g, 0.176 mol) is added dropwise. The mixture is allowed to warm to room temperature and stirred overnight. Water (20 mL) is added, and the solvent is removed by evaporation. The residue is mixed with hexane (300 mL) and the resultant solid is collected by filtration. This solid then is dried under vacuum, yielding compound 72 that is sufficiently pure for subsequent reaction (47.0 g, 83.9% yield). M.P.: 116.0-118.0° C. $^1H$ NMR ($CD_2Cl_2$): δ 5.15 (m, 2H), 2.31 (broad, 2H), 1.91 (m, 4H), 1.31 (m, 32H), 0.92 (t, 6H). $^{13}C$ NMR: 144.06, 109.05, 70.58, 38.77, 32.36, 30.06, 30.04, 29.99, 29.77, 29.65, 26.09, 23.12, 14.29.

2,4-diundecanyl-3,6-dibromothieno[3,2-b]thiophene (73)

Compound 72 (30.0 g, 0.047 mol) is mixed with acetone (200 mL). To this mixture, chromic acid solution (130 mL) is added dropwise at room temperature. The mixture is stirred overnight at room temperature to allow the formation of a solid precipitate. Most of the acetone is then decanted and the rest of the mixture is extracted with ethyl acetate (2×100 mL). The combined organic layers are washed with brine (3×50 mL) and dried over $MgSO_4$. The solvent is evaporated, and the residue is mixed with ethanol (100 mL) and white and pure compound 73 solidified and is collected by filtration (18.4 g, 61.7% yield). M.P.: 120.3-121.5° C. $^1H$ NMR ($CD_2Cl_2$): δ 3.09 (t, 4H), 1.78 (m, 4H), 1.28 (m, 28H), 0.88 (t, 6H). $^{13}C$ NMR: 193.15, 143.62, 143.40, 106.70, 41.74, 32.12, 29.79, 29.72, 29.65, 29.55, 29.35, 24.20, 22.91, 14.11.

Diethyl-3,7-didecylthieno[3,2-b]thieno[2',3':4,5]thieno[2,3-d]thiophene-2,6-dicarboxylate (74)

Compound 73 is mixed with $K_2CO_3$ (16.6 g, 0.12 mol) and N,N-dimethylformamide (100 mL). To this mixture, ethyl 2-mercaptoacetate (6.6 mL, 0.06 mol) is added dropwise at 60° C. The reaction mixture is stirred for 48 hours at 60° C. under nitrogen then is poured into water (500 mL). The resultant solid is collected by filtration. The crude product is then boiled with ethanol (200 mL) and cooled to room temperature. Filtration and drying yielded compound 74 (14.2 g, 72.4% yield). M.P.: 130.5-132.2° C. $^1$H NMR (CD$_2$Cl$_2$): δ 4.36 (q. 4H), 3.15 (t, 4H), 1.73 (m, 4H), 1.27 (m, 34H), 0.87 (m, 6H). $^{13}$C NMR: 163.09, 144.79, 144.29, 135.29, 134.28, 128.54, 61.83, 32.57, 30.32, 30.26, 30.21, 30.07, 30.02, 29.98, 29.79, 23.33, 14.79, 14.49.

3,7-Didecylthieno[3,2-b]thieno[2',3':4,5]thieno[2,3-d]thiophene-2,6-dicarboxylic acid (75)

Compound 74 (14.0 g, 0.021 mol) is mixed with LiOH (1.24 g, in 15 mL water), THF (100 mL), MeOH (20 mL) and a catalytic amount of tetrabutylammonium iodide. This mixture is heated at reflux overnight and most of the solvent is evaporated. The residue is acidified with concentrated HCl (30 mL). The resultant solid is collected by filtration, washed thoroughly with water and vacuum dried to yield compound 75 (12.5 g, 97.4% yield). M.P.: 315.6-318.5° C.

3,7-didecylthieno[3,2-b]thieno[2',3':4,5]thieno[2,3-d]thiophene (70)

Compound 75 (13.5 g, 0.021 mol) is mixed with copper powder (0.9 g) in quinoline (80 mL), and the mixture is heated to 250-260° C. in a Woods metal bath. When no further bubbles of carbon dioxide gas could be detected (about 2 hours), the mixture is allowed to cool to room temperature and hot hexane (400 mL) is added. This mixture is then repeatedly washed in HCl (2N, 4×50 mL). The hexane is partially removed by evaporation, and the resultant solid is collected by filtration and re-crystallized from hexane to afford compound 70 (7.0 g, 60.6% yield). M.P.: 111.0-113.3° C. $^1$H NMR (C$_6$D$_6$): δ 6.53 (s, 2H), 2.51 (t, 4H), 1.64 (m, 4H), 1.27 (m, 28H), 0.89 (t, 6H). $^{13}$C NMR: 141.26, 136.42, 133.17, 132.04, 120.73, 32.31, 30.03, 29.96, 29.90, 29.79, 29.66, 29.04, 23.07, 14.28.

Example 5

Figure 14:
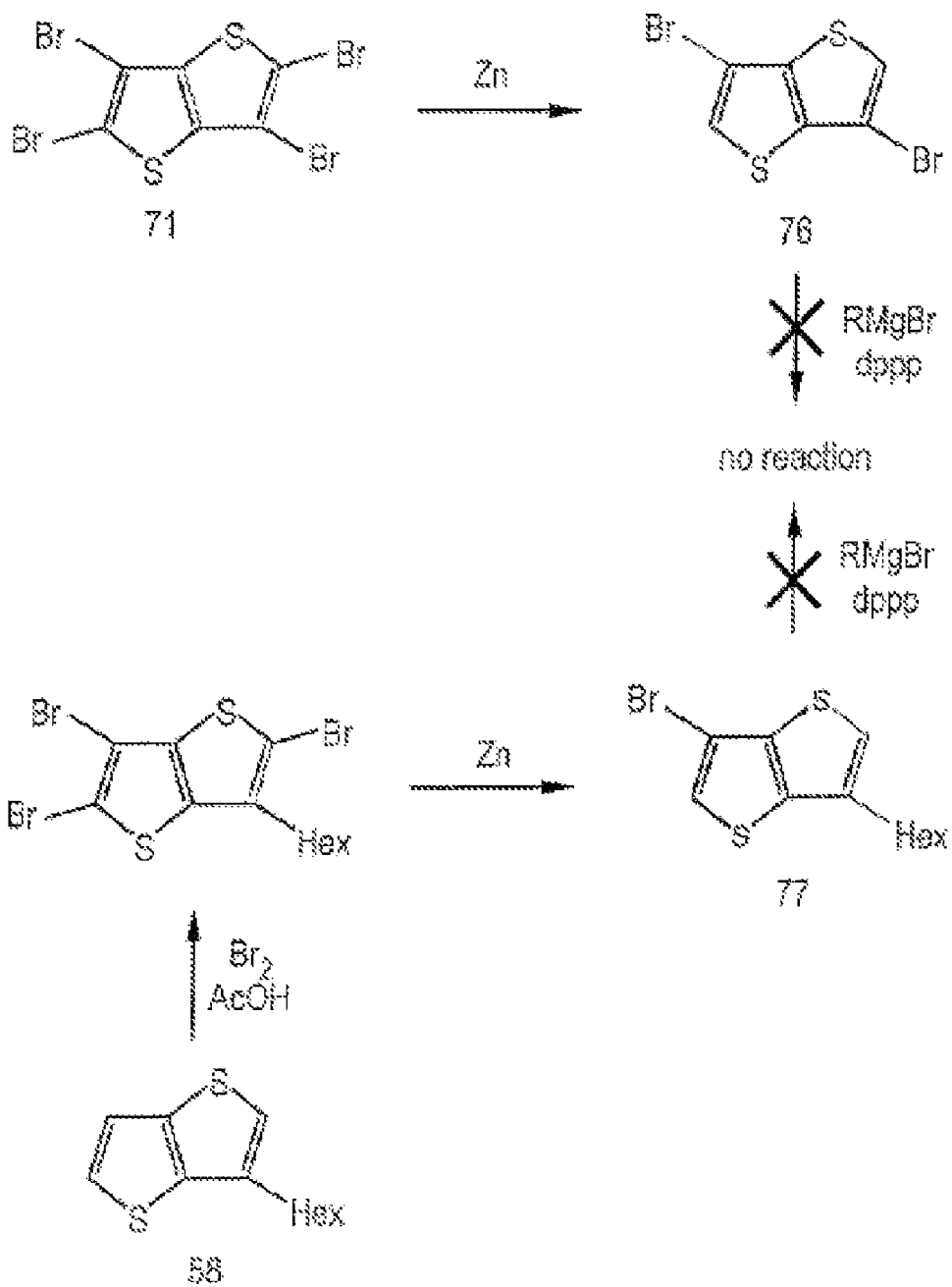
FIG. 14 is a reaction scheme showing the failed synthesis of β-hexyl-substituted thieno[2,3-d]thiophene according to conventional methodologies as described in Example 5.

Attempt to Synthesize β-Substituted thieno[2,3-d]thiophenes Using Conventional Coupling Reactions The reaction scheme of FIG. 14 is followed in an unsuccessful attempt to synthesize β-hexyl-substituted thieno[2,3-d]thiophene. Because the electronic properties of the fused ring systems are much different than those of a simple monocyclic thiophene, the coupling reactions used for the monocyclic thiophenes do not work.

3,6-dibromothieno[3,2-b]thiophene (76, 5.2 g, 0.0175 mol) is dissolved in dry diethyl ether (100 mL), and mixed with [1,3-bis(diphenylphosphino)propane]di-chloronickel (II) (dppp) (0.47 g, 0.05 equivalents). To this solution hexylmagnesium bromide (22.0 mL of 2.0 M solution in diethyl ether, 0.044 mol) is added dropwise. The resulting mixture is heated at reflux for 24 hours. The reaction is monitored by GC/MS. After 24 hours, the starting material has disappeared, but no Grignard addition product had been formed.

3-bromo-6-hexylthieno[3,2-b]thiophene (77, 6.2 g, 0.021 mol) is dissolved in dry diethyl ether (100 mL) and mixed with [1,3-bis(diphenylphosphino)propane]di-chloronickel (II) (dppp) (0.51 g, 0.05 equivalents). To this solution hexylmagnesium bromide (13.3 mL of 2.0 M solution in diethyl ether, 0.027 mol) is added dropwise. The resulting mixture is heated at reflux for 24 hours. The reaction is monitored by GC/MS, and, after 6 hours, the starting material has disappeared, but no Grignard addition product has been formed.

Example 6

Poly(β-Substituted Fused Thiophenes)

Fused thiophene polymers are made using the general procedure described below. This procedure is adapted from Andersson et al., 27 MACROMOLECULES 6506 (1994), herein incorporated by reference in its entirety.

A monomeric α,α'-dihydro β,β'-dialkyl fused thiophene compound (10 mmol) is dissolved in 30 mL chlorobenzene. A suspension of ferric chloride (2.5 mmol) in 20 mL chlorobenzene is added to the monomer solution over half an hour. The mixture is allowed to stir for several (e.g. from 6 to 24) hours at room temperature. It may be desirable to heat the reaction mixture at 80-90° C. for several hours for fused thiophene compounds having larger (e.g. 4 or greater) numbers of rings in their fused ring system. The reaction mixture is then precipitated from 500 mL 95:5 methanol:water. The precipitate is collected by filtration, dissolved in toluene, boiled with concentrated ammonia (3×60 mL), and boiled with ethylenediaminetetraacetic acid (0.05 M in water, 2×50 mL). The organic layer is precipitated from methanol (500 mL); filtration and vacuum drying (70-80° C.) of the product yield the polymeric material: poly(3,6-dihexylthieno[2,3-d]thiophene) (35% yield); poly(3,6-didecylthieno[2,3-d]thiophene (90% yield); poly(3,7-didecylthieno[3,2-b]thieno[2',3':4,5]thieno[2,3-d]thiophene) (80% yield); and poly(3,5-didecyldithieno[3,2-b:2',3'-d]thiophene-4,4-dioxide) (43% yield).

Example 7

Synthesis 2-2, 3-3 and 4-4 Dimer and 5 and 7 Ring Systems

The synthesis 2-2, 3-3 and 4-4 dimers and 5 and 7 ring systems is depicted in FIG. 15.

3,3'-dibromo-6,6'-didecanyl-2,2'-bisthienothiophene (82)

Butyllithium (2.5 M in hexane, 15.6 mL, 0.039 mol) is added dropwise at 0° C. to a flask with diisopropylamine (4.0 g, 0.039 mol) in dry THF (30 mL). The resulting mixture is kept at 0° C. for 15 minutes, then 3-bromo-6-decanylthienylhiophene (81) (14.0 g, 0.039 mol) is added dropwise as a THF solution (30 mL). This mixture is stirred at 0° C. for one hour before copper (II) chloride (6.3 g, 0.047 mol) is added. The dark brown solution is stirred for an additional 12 hours at room temperature. After evaporation of all of the solvent, the residue is boiled in toluene (200 mL), and the solid is filtered. The solution is washed by brine (2×50 mL), water (50 mL) and dried over MgSO$_4$. After the toluene is evaporated, the residue is boiled with ethanol (700 mL) and the solid is collected after cooling. The target compound is collected as a yellow solid crystal powder. Yielded 9.35 g (67%). M.P.: 90.0-91.0° C. $^1$HNMR (CD$_2$Cl$_2$): δ 7.15 (s, 2H), 2.74 (t, 4H), 1.89-1.27 (m, 32H), 0.89 (t, 6H). $^{13}$CNMR: 140.78, 136.25, 133.02, 131.65, 131.23, 120.47, 31.92, 29.61 (overlap), 29.36 (overlap), 28.73, 22.69, 14.11.

3,6-didecanyl-dithieno[2,3-d:2',3'-d']thieno[3,2-b:4,5-b']dithiophene (83)

3,3'-dibromo-6,6'-didecanyl-2,2'-bisthienothiophene (82) (8.6 g, 0.012 mol) is dissolved into THF (100 mL). This solution is cooled to −78° C. under argon. To this solution, butyllithium (9.6 mL, 0.024 mol) is added dropwise and the resulting mixture is stirred at −78° C. After about 30 minutes, bis(phenylsulfonyl)sulfide (3.8 g, 0.012 mol) is added and the solution is stirred overnight at room temperature before the THF is evaporated. The residue is dissolved into hexane (300 mL) and the organic layer is washed with brine (2×100 mL) and water (50 mL). The organic layer is then dried over $MgSO_4$. After evaporating the solvent, the crude product is purified by column chromatography (hot hexane) to give a solid compound. This yellow compound is recrystallized from hexane, yielding 3.2 g (45.3%). M.P.:. 107.7-108.5° C. $^1$HNMR ($CD_2Cl_2$): δ 7.024 (s, 2H), 2.76 (t, 4H), 1.79-1.28 (m, 32H), 0.88 (t, 6H). $^{13}$CNMR: 140.58, 138.96, 135.94, 129.80, 122.86, 105.64, 31.92, 29.77, 29.57, 29.33 (overlap), 28.69, 22.69, 14.11.

Figure 15A:
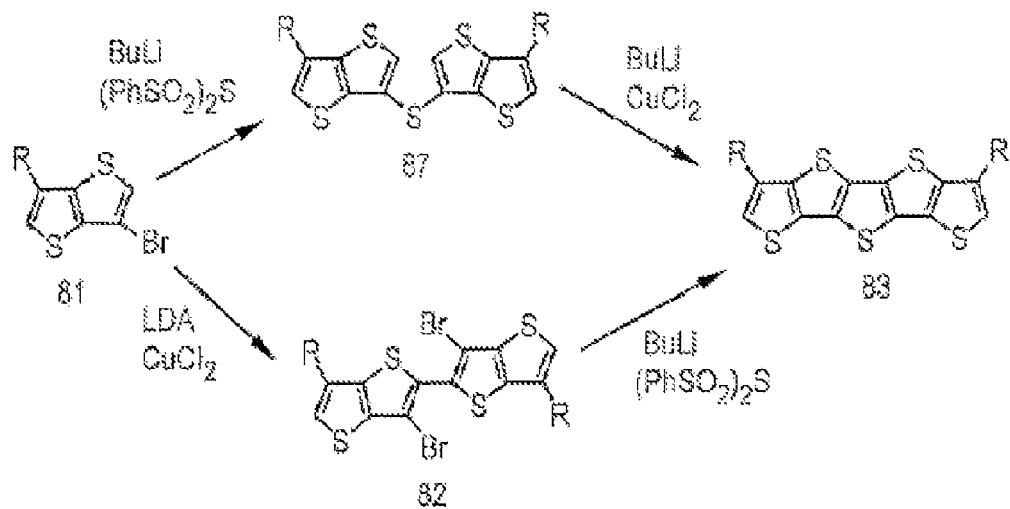
FIG. 15A and FIG. 15B are reaction schemes for the synthesis 2-2 and 3-3 dimers and 5- and 7-ring systems according to Example 7.

Referring to FIG. 15A, 83 can also be prepared by the cyclization of 87 with butyllithium and copper chloride.

3,3'-dibromo-5,5'-didedecanyl-2,2'-bisdithieno[3,2-b:2',3'-d]thiophene (85)

Butyllithium (2.5 M in hexane, 4.4 mL, 0.011 mol) is added dropwise at 0° C. to a flask with diisopropylamine (1.13 g, 0.011 mol) in dry THF (30 mL). The resulting mixture is kept at 0° C. for 15 minutes, then 3-bromo-5-decanyl-dithieno[3,2-b:2',3'-d]thiophene (84) (4.61 g, 0.011 mol) dissolved into THF (40 mL) is added dropwise. This mixture is stirred at 0° C. for one hour before copper (II) chloride (1.77 g, 0.013 mol) is added. This dark green solution is stirred for an additional 12 hours at room temperature. After evaporating all of the solvent, the residue is boiled with toluene (2×100 mL) and the solid is filtered. After evaporating all of the toluene, the residue is boiled with toluene (200 mL) and cooled to room temperature. The crystalline solid is collected after cooling. Yield 2.0 g. (43.8%). M.P.: 140.2-141.1° C. $^1$HNMR ($CD_2Cl_2$): δ 7.11 (s, 2H), 2.78 (t, 4H), 1.75-1.28 (m, 32H), 0.86 (t, 6H).

3,7-didecanyl-bisdithieno{[3,2-b;4,5-d][2',3'-b;4',5'-d]}thiophene (86)

3,3'-dibromo-5,5'-didecanyl-bisdithienothiophene (85) (3 g, 3.62 mmol) is dissolved in dry tetrahydrofuran (80 mL) and cooled to −78° C. To this mixture, butyllithium (7.23 mmol, 2.9 mL) is added dropwise under argon. The resulting mixture is stirred at −78° C. for one hour before bis(phenylsulfonyl) sulfide (1.15 g, 3.62 mmol) is added through a solid addition funnel. The resulting mixture is stirred and slowly warmed up to room temperature overnight. After evaporating the THF, the residue is refluxed with water (200 mL) and filtered. The solid is then washed by methanol (2×50 mL) and refluxed with toluene (200 mL). The hot toluene solution is filtered to remove undissolved solid. After evaporating the toluene, the solid is re-dissolved into toluene (70 mL) and cooled to room temperature to produce brown-yellow needles of the target compound (1.68 g, 66.3% yield). M.P.: 140.2-141.1° C. $^1$HNMR ($CD_2Cl_2$): δ 7.11 (s, 2H), 2.78 (t, 4H), 1.79-1.28 (m, 32H), 0.88 (t, 6H).

Figure 15B:
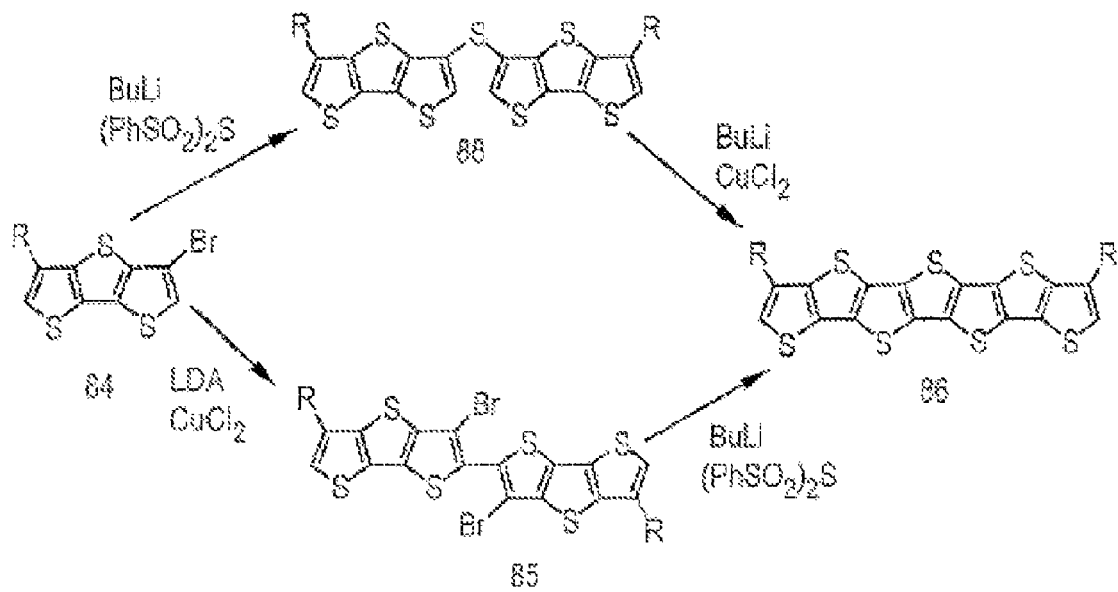

Referring to FIG. 15B, 86 can also be prepared by the cyclization of 88 with butyllithium and copper chloride.

Example 8

Synthesis of Tetraalkylsubstituted Thienothiophene Dimer

Figure 16:
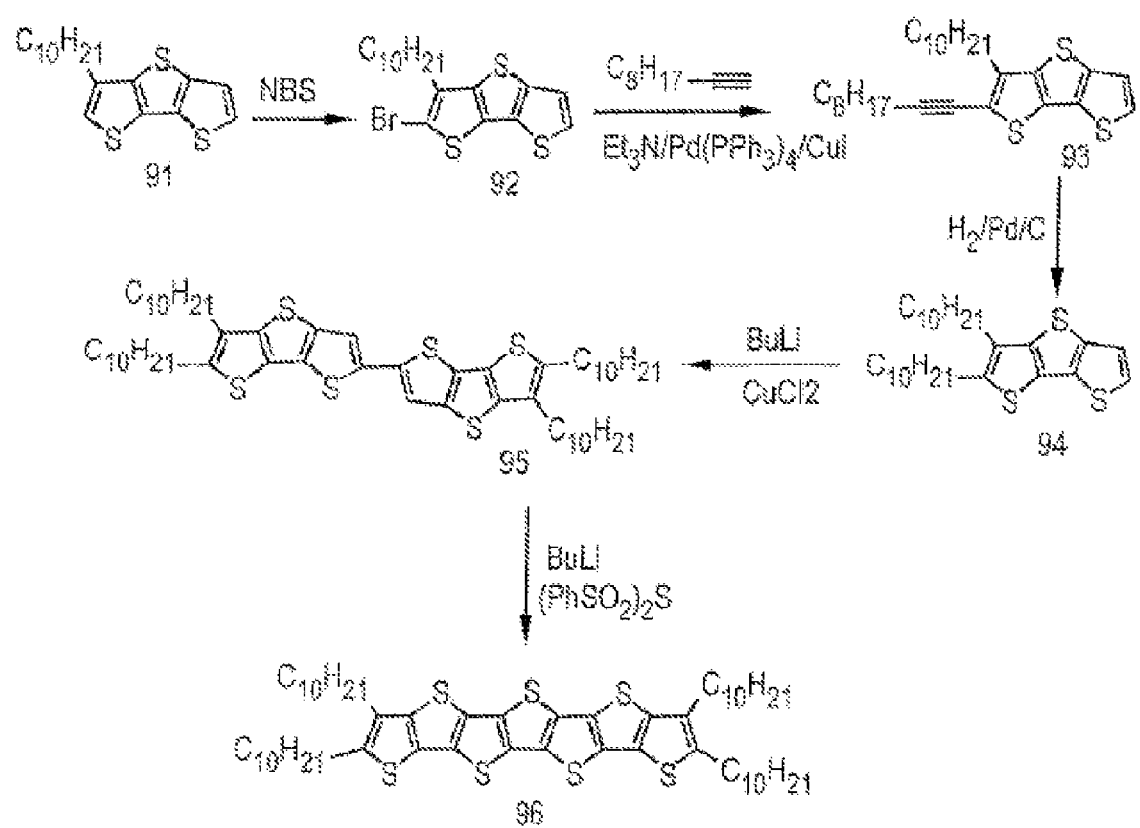
FIG. 16 is a reaction scheme for the synthesis of a seven-ring tetraalkylsubstituted thienothiophene according to Example 8.
Figure 17:
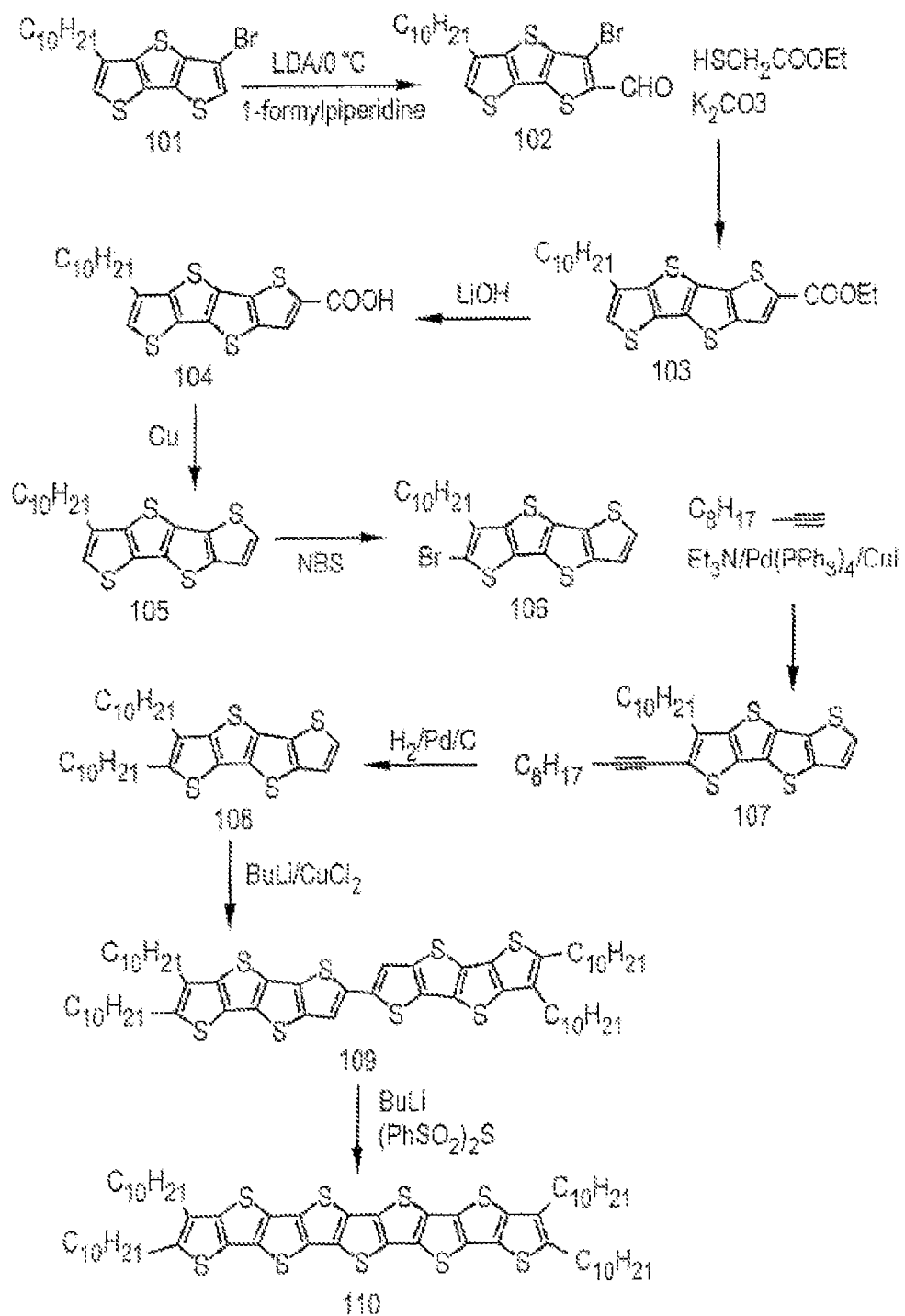
FIG. 17 is a reaction scheme for the synthesis of a nine-ring tetraalkylsubstituted thienothiophene according to Example 8.

The synthesis of three-ring and four-ring tetraalkylsubstituted thienothiophene dimers is depicted in FIGS. 16 and 17, respectively.

A. Three Ring Dimer

2-bromo-3-decanyldithieno[3,2-b:2',3'-d]thiophene (92)

3-decanyldithieno[3,2-b:2',3'-d]thiophene (91) (9.03 g, 0.027 mol) is dissolved in DMF (100 mL). To this solution, N-bromosuccinimide (NBS) (4.78 g, 0.027 mol) in DMF (50 mL) is added dropwise in the dark and under argon. The resulting mixture is stirred at 0° C. for about three hours or until GC/MS shows a single peak at 415. This solution is poured into water (500 mL) and the organic solution is extracted with hexane (3×100 mL). The combined organic solutions are washed with brine (2×50 mL) and water (50 mL). After drying over $MgSO_4$, the hexane is evaporated. The crude product is purified by column chromatography and eluted with hexane to yield the target compound (10.1 g, 90.2% yield). $^1$HNMR ($CD_2Cl_2$): δ 7.39 (d, 1H), 7.29 (d, 1H), 2.74 (t, 2H), 1.74-1.33 (m, 16H), 0.89 (t, 3H). $^{13}$CNMR: 140.89, 140.63, 136.00, 131.55, 129.22, 126.58, 121.04, 108.89, 32.31, 29.94, 29.73 (overlap), 29.35, 28.49, 23.09, 14.27.

3-decanyl-6-dec-1-ynyldithieno[3,2-b:2',3'-d]thiophene (93)

2-bromo-3-decanyldithieno[3,2-b:2',3'-d]thiophene (92) (4.16 g, 0.01 mol) is mixed with 1-decyne (3.6 g, 0.026 mol), tetrakis(triphenylphosphine)palladium (0.58 g, 0.5 mmol) and copper(I) iodide (0.19 g, 1.0 mmol) in triethylamine (80 mL). This mixture is bubbled with nitrogen for 5 minutes and then heated to 130° C. under argon for 16 hours. Triethylamine is evaporated and hexane (150 mL) is added. The mixture is filtered to remove solid salts and the organic layer is washed with 1M hydrochloric acid (50 mL) and brine (50 mL), then dried over $MgSO_4$. The solvent is removed in vacuo, and the residue is purified by chromatography on silica gel eluting with hexane to yield the target compound (3.87 g, 93.0% yield). $^1$HNMR ($CD_2Cl_2$): δ 7.36 (d, 1H), 7.30 (d, 1H), 2.82 (t, 2H), 2.49 (t, 2H), 1.63-1.27 (m, 28H), 0.88 (m, 6H).

2,3-didecanyldithieno[3,2-b:2',3'-d]thiophene (94)

3-decanyl-6-dec-1-ynyldithieno[3,2-b:2',3'-d]thiophene (93) (36.0 g, 0.076 mol) is dissolved into ethyl acetate (60 mL), and 5% Pt/C (9.0 g) is added to the solution. The mixture is stirred under a $H_2$ atmosphere (90 psi) for 24 hours and then filtered. After removal of the ethyl acetate, the residue is purified by chromatography on silica gel eluted with hexane to produce the target compound (29.0 g, 79.9% yield). $^1$HNMR ($CD_2Cl_2$): δ 7.29 (d, 1H), 7.27 (d, 1H), 2.80 (t, 2H), 2.67 (t, 2H), 1.68-1.27 (m, 32H), 0.88 (m, 6H). $^{13}$CNMR. 142.88, 140.75, 139.82, 131.69, 131.37, 126.69, 125.04, 120.94, 32.16, 29.85 (m, overlap), 22.93, 14.11.

5,6,5'6'-tatradecanyl-2,2'-bisdithieno[3,2-b:2',3'-d]thiophene (95)

Butyllithium (4.5 mL, 0.011 mol) is added dropwise under argon at room temperature to a hexane solution of 2,3-didecanyldithieno[3,2-b:2',3'-d]thiophene (94) (5.16 g, 0.011 mol) and N,N,N',N',-tetramethylethylenediamine (TMEDA) (1.25 g, 0.011 mol). The resulting mixture is refluxed for one hour before copper (II) chloride powder is added to the reaction and this mixture is then stirred overnight. The hexane is then removed in vacuo and the residue is boiled with toluene (80 mL), and the resulting residue is removed by filtration. The organic layer is washed with brine (2×30 mL) and water (30 mL) and dried over $MgSO_4$. After removal of the toluene, the yellow solid is boiled with acetone (400 mL) and cooled to room temperature to produce crystalline target compound (1.26 g, 24.5% yield). $^1$HNMR ($CD_2Cl_2$): δ 7.43 (s, 2H), 2.89 (t, 4H), 2.73 (t, 4H), 1.76-1.34 (m, 64H), 0.93 (m, 12H). $^{13}$CNMR ($C_6D_{12}$): 143.28, 141.09, 140.94, 138.12, 131.66, 131.41, 127.91, 117.18, 32.74, 32.63, 30.44, 30.39, 30.32, 30.29, 30.13, 29.86, 28.58, 23.41, 14.25.

Referring to FIG. 16, 96 can also be prepared by the cyclization of 95 with butyllithium and bis(phenylsulfonyl) sulfide.

B. Four Ring Dimer

2-Formyl-3-bromo-5-decanyldithieno[3,2-b:2',3'-d]thiophene (102)

Butyllithium (2.5 M in hexane, 10.9 mL, 0.0273 mol) is added dropwise at 0° C. to a flask with diisopropylamine (2.76 g, 0.027 mol) in dry THF (100 mL). The resulting mixture is kept at 0° C. for 15 minutes. 3-bromo-5-decanyldithieno[3,2-b:2',3'-d]thiophene (101) (11.33 g, 0.0273 mol) is dissolved into THF (60 mL) and added dropwise to the reaction. This mixture is kept at 0° C. for one hour before 1-formylpiperidine is added. The resulting mixture is stirred overnight and the THF is then removed. The residue is washed with 10% hydrochloric acid (30 mL) and water (3×100 mL). The solid target compound is purified by crystallization from ethyl alcohol (100 mL) (8.80 g, 72.8% yield). M.P.: 65.5-67.2° C.

2-carboxylic ethyl ester-5decanyldithieno[2,3-d:2',3'-d']thieno[3,2-b:4,5-b']dithiophene (103)

2-Formyl-3-bromo-5-decanyldithieno[3,2-b:2',3'-d]thiophene (102) (8.80 g, 0.02 mol) is dissolved into DMF (100 mL) and mixed with potassium carbonate (9.66 g, 0.07 mol). A catalytic amount 18-crown-6 ether is used as catalyst. To this solution, ethyl thioglycolate (2.52 g, 0.021 mol) is added dropwise at 60-70° C. This mixture is stirred at this temperature overnight and after checking the GC/MS for reaction completion, the mixture is poured into water (500 mL). The solid formed from the water solution is removed by filtration. The solid is then washed with water (2×200 mL) and methanol (200 mL). GC/MS shows a single peak at 465. After drying in vacuo, the target compound is used without further purification. (8.0 g, 86% yield). M.P.: 59.4-62.0° C.

2-carboxylic-acid-5-decanyldithieno[2,3-d:2',3'-d']thieno[3,2-b:4,5-b']dithiophene (104)

2-carboxylic ethyl ester-3-bromo-5decanyldithieno[2,3-d:2',3'-d']thieno[3,2-b:4,5-b']dithiophene (103) (9.3 g, 0.02 mol) is dissolved in THF (100 mL). To this solution, methanol (20 mL) and LiOH (10% solution, 7 mL) are added, along with a sufficient amount of tetrabutylammonium iodide as a catalyst. The mixture is refluxed overnight, then about ⅔ of the solvent is removed and the residue is poured into concentrated HCl (100 mL). The solid is collected by filtration and washed with water until neutral. After drying, 6.06 grams of target compound is obtained (69.3% yield). M.P.: 225-227° C.

5-decanyldithieno[2,3-d:2',3'-d']thieno[3,2-b:4,5-b']dithiophene (105)

2-carboxylic acid-5-decanyldithieno[2,3-d:2',3'-d']thieno[3,2-b:4,5-b']dithiophene (104) (6.06 g, 0.014 mol) is dissolved into quinoline (80 mL) and then copper powder (0.62 g, 9.7 mmol) is also added to the mixture. The mixture is heated to 240-260° C. and maintained at this temperature until no gas bubbles are observed (about one hour). The mixture is cooled to room temperature and poured into 30% HCl water solution (300 mL). The organic solution is extracted with hexane (150 mL) and washed with 10% HCl several times to remove the quinoline from the organic layer. The organic layer is then dried over $MgSO_4$. After removing the solvent, the residue is recrystallized from ethanol to produce 4.44 g of target compound (81.3% yield). M.P.: 88.3-89.6° C. $^1$HNMR ($CD_2Cl_2$): δ 7.38 (d, 1H), 7.32 (d, 1H), 6.99 (m, 1H), 2.73 (t, 2H), 1.77 (m, 2H), 1.35-1.27 (m, 14H), 0.87 (t, 3H). $^{13}$CNMR: 141.29, 140.59, 136.72, 133.51, 132.32, 132.27, 131.51, 126.29, 121.15, 121.02, 32.32, 30.00, 29.96, 29.78 (overlap), 29.73, 29.11, 23.09, 14.28.

2-Bromo-3-decanyldithieno[2,3-d:2',3'-d']thieno[3,2-b:4,5-b']dithiophene (106)

NBS (2.01 g, 0.0113 mol) in DMF (30 mL) is added dropwise in the dark at 0° C. to 5-decanyldithieno[2,3-d:2',3'-d']thieno[3,2-b:4,5-b']dithiophene (105) (5.56 g, 0.0113 mol) in dry DMF (50 mL). The resulting mixture is stirred for two hours and poured into water (500 mL). The solid is filtered and washed by water several times and ethanol (200 mL) is used to recrystallize the crude compound to give 5.06 g (94.9% yield). $^1$HNMR ($CD_2Cl_2$): δ 7.43 (d, 1H), 7.34 (d, 1H), 2.77 (t, 2H), 1.74 (m, 2H), 1.36-1.27 (m, 16H), 0.87 (t, 3H). $^{13}$CNMR: 140.87, 139.54, 135.98, 133.31, 132.11, 131.70, 130.26, 126.77, 121.23, 109.03, 32.32, 29.99, 29.92, 29.75, 29.66, 29.36, 28.50, 23.09, 14.28.

2-dec-1-ynyl-3-decanyldithieno[2,3-d:2',3'-d']thieno[3,2-b:4,5-b']dithiophene (107)

2-Bromo-3-decanyldithieno[2,3-d:2',3'-d']thieno[3,2-b:4,5-b']dithiophene (2.16 g, 4.6 mmol) (106) is mixed with 1-decyne (1.27 g, 9.2 mmol), tetrakis(triphenylphosphine) palladium (0.27 g, 0.23 mmol) and copper(I) iodide (0.087 g, 0.46 mmol) in triethylamine (50 mL). This mixture is bubbled with nitrogen for 5 minutes and then heated to 130° C. under argon for 16 hours. The triethylamine is evaporated and hexane (150 mL) is added. This mixture is filtered to remove solid salts. The organic layer is washed with 1M hydrochloric acid (50 mL) and brine (50 mL), then dried over $MgSO_4$. The solvent is removed in vacuo, and the residue is purified by chromatography on silica gel eluted with hexane to produce the target compound (2.3 g, 90.2% yield). $^1$HNMR ($CD_2Cl_2$): δ 7.41 (d, 1H), 7.33 (d, 1H), 2.84 (t, 2H), 2.23 (t, 2H), 1.73-1.27 (m, 28H), 0.89 (m, 6H).

2,3-didecanyldithieno[2,3-d:2',3'-d']thieno[3,2-b:4,5-b']dithiophene (108)

2-dec-1-ynyl-3-decanyldithieno[2,3-d:2',3'-d']thieno[3,2-b:4,5-b']dithiophene (107) (2.2 g, 4.15 mmol) is dissolved into ethyl acetate (30 mL) and to this solution, 5% Pt/C (0.5 g)

is added. The mixture is stirred under a H₂ atmosphere (90 psi) for 24 hours, then filtered. After removal of the ethyl acetate, the residue is purified by chromatography on silica gel eluted with hexane to produce the target compound (2.00, 90.5% yield). M.P.: 50.9-52.5° C. ¹HNMR (CD₂Cl₂): δ 7.41 (d, 1H), 7.33 (d, 1H), 2.83 (t, 2H), 2.50 (t, 2H), 1.73-1.26 (m, 32H), 0.87 (m, 6H). ¹³CNMR: 140.85, 140.40, 139.93, 133.38, 133.14, 132.22, 129.69, 121.17, 120.09, 98.92, 32.29, 32.25, 29.99, 29.94, 29.72, 29.63, 29.52, 29.33, 29.18, 29.06, 28.94, 23.05, 14.23.

Referring to FIG. 17, 109 can be prepared by coupling 108 with butyllithium and copper chloride. The cyclization of 109 to produce 110 can be accomplished by reacting 109 with butyllithium and bis(phenylsulfonyl)sulfide.

Example 9

Synthesis of Polymers Containing Fused Thiophene Moiety

Poly-3,6-dihexyl-thieno[3,2-b]thiophene (PDC6FT2) and Poly-3,6-didecanyl-thieno[3,2-b]thiophene (PDC10FT2)

The monomer, 3,6-dihexyl-thieno[3,2-b]thiophene (3.08 g, 0.01 mol) is dissolved into chlorobenzene. A suspension of FeCl₃ in chlorobenzene is added to the monomer solution within a half hour. The final concentration for the monomer and FeCl₃ is 0.05 and 0.2 M, respectively. The mixture is stirred for 6-24 hours at room temperature. For larger ring sizes, the mixture can be heated to 80-90° C. for several hours. The polymer solution is poured into 5% water methanol solution and a precipitate formed. The polymer is collected through filtration and re-dissolved into toluene. The toluene solution then is boiled with concentrated ammonia (3×60 mL) and then boiled twice with ethylenediaminetetraacetic acid (EDTA) (0.05 M in water) (2×50 mL). The resulting toluene is slowly added dropwise to methanol (500 mL) to precipitate polymer. After filtration, the polymer is dried in vacuum oven (70-80° C.) overnight. Yields of PDC6FT2 and PDC10FT2 are 35% and 90%, respectively.

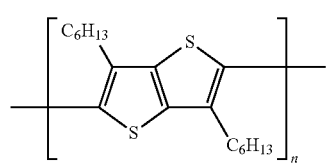

PDC6FT2

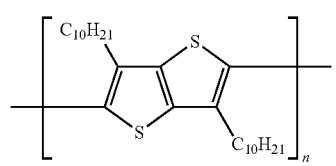

PDC10FT2

The method above is also used to produce the polymers PDC10FT4 (80% yield) and PDC10FTS3 (43% yield)

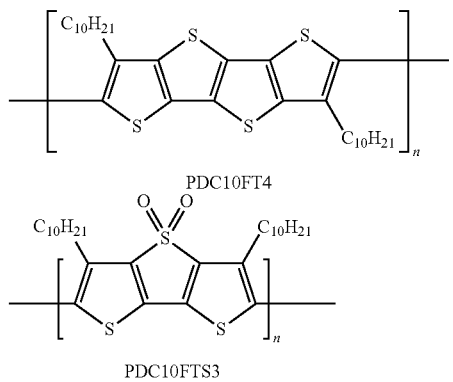

Example 10

Synthesis of Bithiophene and Fused Thiophene Copolymers 2,6-Dibromo-3,5-didecanyldithieno[3,2-b:2'3'-d] thiophene (1.0 g, 1.57 mmol), 2,5'-distannyltrimethyl-bithiophene (0.772 g, 1.57 mmol) and tetrakis(triphenylphosphine)palladium(0) (0.095 g, 0.082 mmol) are dissolved in chlorobenzene (30 mL) under argon. The resulting mixture is heated to 150° C. under argon for 14 hours before being precipitated into methanol (400 mL). The collected solid polymer is washed with acetone (100 mL) and extracted using acetone in a Soxhlet extractor. The solid polymer then is dissolved in chlorobenzene (100 mL) and filtered through a glass filter. After evaporating most of the chlorobenzene, the polymer as shown below is precipitated from methanol (300 mL) again. The red polymer powder is dried under vacuum to give 0.9 grams (90.1% yield).

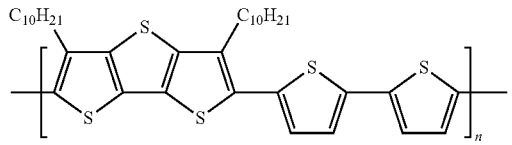

2,7-Dibromo-3,6-didecanylpentathienoacene (0.89 g, 1.19 mmol), 2,5'-distannyltrimethyl-bithiophene (0.59 g, 1.57 mmol) and tetrakis(triphenylphosphine)palladium(0) (0.072 g, 0.062 mmol) are reacted as described above. The polymer is extracted by hexane in a Soxhlet extractor. The final polymer as shown below is dried over vacuum to give 0.8 grams (89% yield).

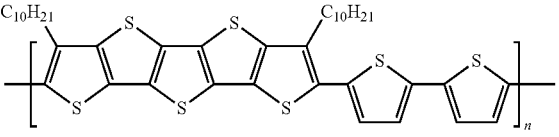

2,8-Dibromo-3,7-didecanyl thieno[3,2-b]thieno[2',3':4,5] thieno[2,3-d]thiophene (1.0 g, 1.45 mmol), 1,4-ditrimethyl-stannylbenzene (0.59 g, 1.45 mmol) and tetrakis(triphenylphosphine)palladium(0) (0.084 g, 0.073 mmol) are reacted as described above. The polymer as shown below is dried under vacuum to give 0.82 grams (93.2% yield).

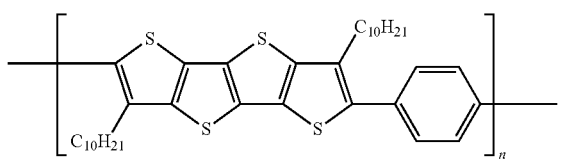

Example 11

Synthesis of Fused Thiophene-Diketopyrrolopyrrole Moieties and Polymers

The incorporation of fused thiophene moieties into polymers further containing diketopyrrolopyrrole ("DPP") moieties provides several advantages: 1) The lack of β-hydrogens on the fused thiophene moieties would make the DPP-conjugated copolymer structures more stable; 2) The potential to put large alkyl-based R-groups on the fused thiophene moieties allows for improvements in the solubility of the copolymer; 3) the fused thiophene systems consist of larger conjugation units, which may improve the electronic and optical properties of the DPP system.

Fused Thiophene Synthesis 2,6-dibromo-3,7-diheptadecylthieno[3,2-b]thieno[2',3':4,5]thieno[2,3-d]thiophene can be synthesized as described herein. A mixture of 2,6-di(trimethylstannyl)-3,7-diheptadecylthieno[3,2-b]thieno[2',3':4,5]thieno[2,3-d]thiophene (16.0 g, 18.0 mmol) in hexane (500 mL) is cooled to 0° C. and n-butyl lithium (36 mL, 72 mmol) (2 M in hexane) is added dropwise with stirring. After complete addition, the mixture is allowed to warm to room temperature and then heated to reflux for 4 h. The resulting solution is cooled to 0° C. then trimethyltin chloride (90 mL, 90 mmol) (1M in THF) is added dropwise. After complete addition, the mixture is allowed to warm to room temperature and stirred for a further 2 h. Ice water (100 g) is added with vigorous stirring to quench the reaction. The hexane and THF are removed under reduced pressure and the residue is suspended in water (500 mL) and stirred for 1 h. The suspension is filtered and the solid re-suspended in methanol (500 mL) and stirred for a further 1 h. The suspension is filtered and the solid re-suspended in ethanol (500 mL) and stirred for a final 1 h. The suspension is filtered and the product is recrystallized from a mixture of ethylacetate (25%) and acetone (75%) (300 mL) giving the product, 2,6-di(trimethylstannyl)-3,7-diheptadecylthieno[3,2-b]thieno[2',3':4,5]thieno[2,3-d]thiophene, thiophene ("P2TDC17FT4") as shown in FIG. 20, (17.6 g, 93% yield) as a white solid. M.P.: 78-79° C.; $^1$HNMR (CD$_2$Cl$_2$, 300 MHz): δ 0.44 (18H, s), 0.88 (6H, t, J=7.1), 1.17-1.47 (56H, m), 1.67-1.82 (4H, m), 2.75 (4H, t, J=7.8); $^{13}$CNMR (CD$_2$Cl$_2$, 75 MHz): −7.9 (6C), 14.1 (2C), 22.7 (2C), 22.7 (2C), 29.2 (2C), 29.3 (2C), 29.6 (20C), 29.9 (2C), 31.5 (2C), 121.0 (2C), 126.0 (2C), 126.1 (2C), 129.0 (2C), 138.0 (2C); m/z (EL) 1056.4 [M]$^+$; Anal. Calc. for C$_{50}$H$_{88}$S$_4$Sn$_2$: C, 56.93; H, 8.41; S, 12.16. Found: C, 57.18; H, 8.17; S.

Dipyrrolopyrole Moiety Synthesis

The formation of the dipyrrolopyrole moiety can be done via the reaction scheme shown in Tieke et al., Beilstein, J. ORG. CHEM. 830 (2010), herein incorporated by reference in its entirety, and is described in FIG. 21. Formation of the bromothienyl-DPP synthesis is based on literature procedures. See, e.g., Tamayo et al., 112 J. PHYS. CHEM. 15543-52 (2008) and Huo et al., 42 MACROMOLECULES 6564-71 (2009), both herein incorporated by reference in their entireties.

Figure 21:
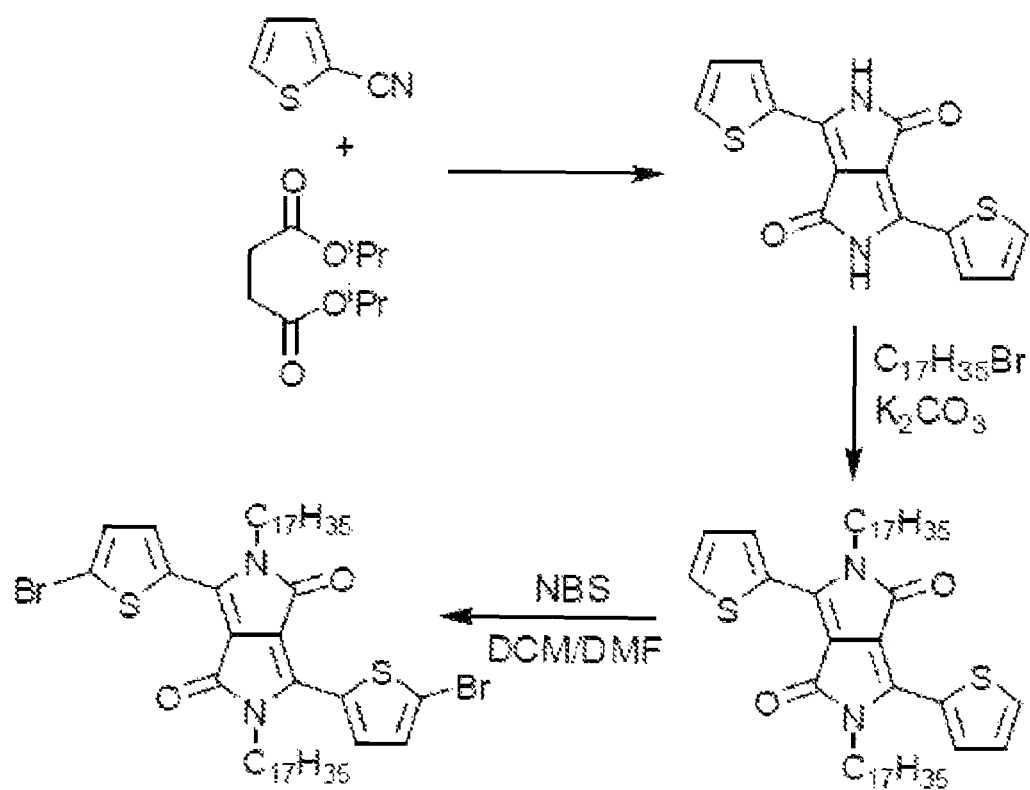
FIG. 21 describes the reaction scheme to produce bis-bromothienyl-DC17DPP (diketopyrrolopyrrole="DPP").
Figure 22:
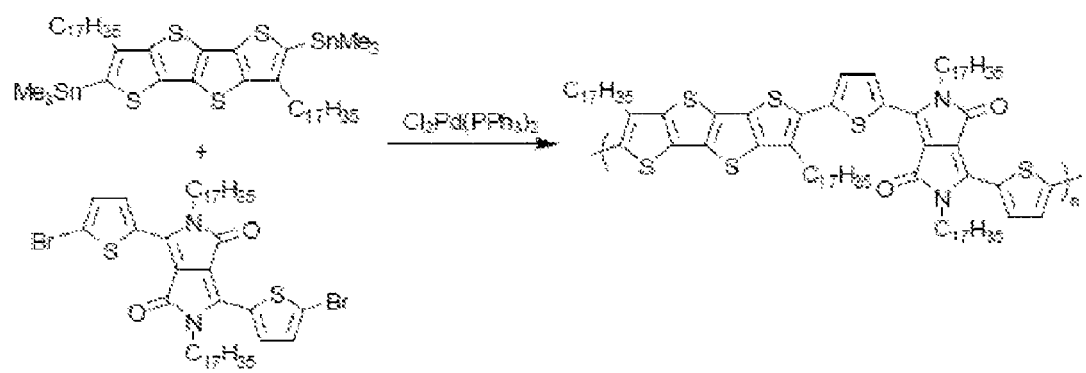
FIG. 22 describes the reaction scheme for coupling bis-tin-substituted FT4 (FT4=four-membered fused thiophene) to bis-bromothienyl-DC17DPP via a palladium-catalyzed Stille-type coupling.

FIG. 21 shows the synthesis of a specific bromothienyl-DPP. Thiophene-carbonitrile and diisopropyl succinate are combined to form a thiophene substituted DPP. This is done in tert-amyl alcohol, with a yield of 82%. The basic thienyl DPP is then N-alkylated using a straight chain alkyl bromide (88% yield), followed by α-bromination of the thiophene groups (90% yield) to make it suitable as a Stille coupling co-monomer. The final material (bromothienyl-DC17DPP) is purified by recrystallization from chloroform giving a 65% overall yield for the three steps.

As a specific example embodiment, potassium tert-butoxide (67.4 g, 0.60 mol) and tert-amyl alcohol (400 mL) are added to a nitrogen-protected oven-dried three-neck round-bottom flask equipped with a mechanical stirrer, a thermometer and a reflux condenser. The mixture is heated to 105° C. for 1.5 h and to this mixture is added 2-thiophenenitrile (55.2 g, 0.50 mol) and the stirring continued at 105° C. for 30 min. A mixture of diisopropyl succinate (40.4 g, 0.20 mol) in tert-amyl alcohol (60 mL) is added dropwise over a period of 3 h with rapid stirring. The mixture is then stirred at 105° C. for a further 2 h, then cooled to 50° C., at which point a mixture of methanol (300 mL) and water (80 mL) is added. The reaction mixture is heated at reflux for 45 min before cooling to room temperature. The mixture is poured over 500 g of ice, then concentrated hydrochloric acid (35% aq) (150 mL) and methanol (750 mL) are added and the mixture is stirred for 45 min. The mixture is filtered and the solid is washed with methanol (200 mL). The solid is then suspended in water (1 L) and stirred for 30 min before being filtered again. This suspension in water, stirring and filtration is repeated a further three times. After filtering for the last time, the solid is oven dried at 80° C. for 16 h, then dried under vacuum to give the product, 3,6-bis(thiophen-2-yl)-2H,5H-pyrrolo[3,4-c]pyrrole-1,4-dione, (49.7 g, 82% yield) as a red solid. This compound is used without further purification. $^1$HNMR (d$_6$-DMSO, 300 MHz): δ 7.27 (2H, t, J=3.0), 7.89 (2H, dd, J$_1$=6.0, J$_2$=3.0), 8.23 (2H, d, J=3.0), 11.00 (2H, s); $^{13}$CNMR (d$_6$-DMSO, 75 MHz): δ 113.6 (2C), 127.1 (2C), 128.3 (2C), 130.5 (2C), 136.6 (2C), 142.6 (2C), 168.2 (2C); m/z (EI$^+$) 300.0 [M]$^+$; Anal. Calc. for C$_{14}$H$_8$N$_2$O$_2$S$_2$: C, 55.98; H, 2.68; N, 9.33; S, 21.35.

Next, N-bromosuccinimide (6.33 g, 35.6 mmol) is added to a solution of 2,5-diheptadecyl-3,6-bis(thiophen-2-yl)pyrrolo[3,4-c]pyrrole-1,4-dione (13.0 g) in chloroform (200 mL) pre-heated to 60° C. in a 1 L flask, wrapped in aluminum foil to exclude light. The reaction is monitored by TLC and stopped as soon as no more mono-brominated species is observed (approximately 30 min), by pouring into methanol (600 mL) stirring in an ice bath. The mixture is filtered and the solid is washed with methanol (2×200 mL) then dried under vacuum. The crude product is recrystallized from chloroform (200 mL) to give the product, 3,6-bis(5-bromothiophen-2-yl)-2,5-diheptadecylpyrrolo[3,4-c]pyrrole-1,4-dione, (14.2 g, 90%) as a dark red solid.

DPP-FT Synthesis

The fused thiophene and diketopyrrolpyrrole moieties may be combined via any standard coupling reaction, such as a Stille coupling reaction. See He et al. 21 ADV. MATER. 2007-2022 (2009), hereby incorporated by reference in its entirety. As shown in FIG. 22, 3,6-bis(5-bromothiophen-2-yl)-2,5-diheptadecylpyrrolo[3,4-c]pyrrole-1,4(2H,5H)-dione is combined with 2,6-bis(trimethylstannyl)-3,7-diheptadecylthieno[3,2-b]thieno[2',3':4,5]thieno[2,3-d]thiophene in N,N-dimethylformamide in the presence of the catalyst bis(triphenylphosphine)palladium(II)dichloride to form poly[(3,7-diheptadecylthieno[3,2-b]thieno[2',3':4,5]thieno[2,3-d]thiophene-2,6-diyl) [2,5-d]heptadecyl-3,6-di(thiophen-2-yl)pyrrolo[3,4-c]pyrrole-1,4(2H,5H)-dione]-5,5'-diyl ("PTDC17DPPTDC17FT4"). The reaction may be done under nitrogen. The reaction in FIG. 22 uses palladium(II) catalyst as it showed good reliability, but palladium(O=0) based catalysts such as tetrakistriphenylphosphine palladium (0) may also be used.

As another example, to a 35 mL microwave reaction vessel equipped with a magnetic stir bar are added 2,6-di(trimethylstannyl)-3,7-diheptadecylthieno[3,2-b]thieno[2',3':4,5]thieno[2,3-d]thiophene (1 g), 3,6-bis(5-bromothiophen-2-yl)-2,5-diheptadecylpyrrolo[3,4-c]pyrrole-1,4-dione (0.860 g, 0.948 mmol), tris(dibenzylideneacetone)dipalladium(0) (17.3 mg, 18.9 mmol) and o-tolyl phosphine (23.0 mg, 75.6 µmol). The reaction vessel and cap are introduced into a nitrogen glovebox, where toluene (20 mL) is added and the cap affixed to the vessel. The vessel is then removed from the glovebox and the reaction microwaved at 160° C. for 2 h. The mixture is cooled to 50° C. before release from the microwave reactor, then poured into a stirring mixture of methanol and acetylacetone (200 mL+200 mL). Hydrochloric acid (2 mL, 35% aq) is added and the mixture stirred for 16 h. The mixture is filtered and the polymer placed into a glass with glass frit Soxhlet thimble. The polymer is extracted in a Soxhlet apparatus with acetone (250 mL) for 24 h, then hexanes (250 mL) for 24 h. The polymer is then extracted from the Soxhlet apparatus into chloroform (250 mL). The chloroform solution is poured into methanol (400 mL) with rapid stirring, followed by moderate stirring for 20 min. The polymer is then filtered from the mixture and dried under vacuum to give the product, poly[(3,7-diheptadecylthieno[3,2-b]thieno[2',3':4,5]thieno[2,3-d]thiophene-2,6-diyl)[2,5-d]heptadecyl-3,6-di(thiophen-2-yl)pyrrolo[3,4-c]pyrrole-1,4-dione]-5,5'-diyl] (1.36 g, 97%) as a dark green solid.

Figure 23:
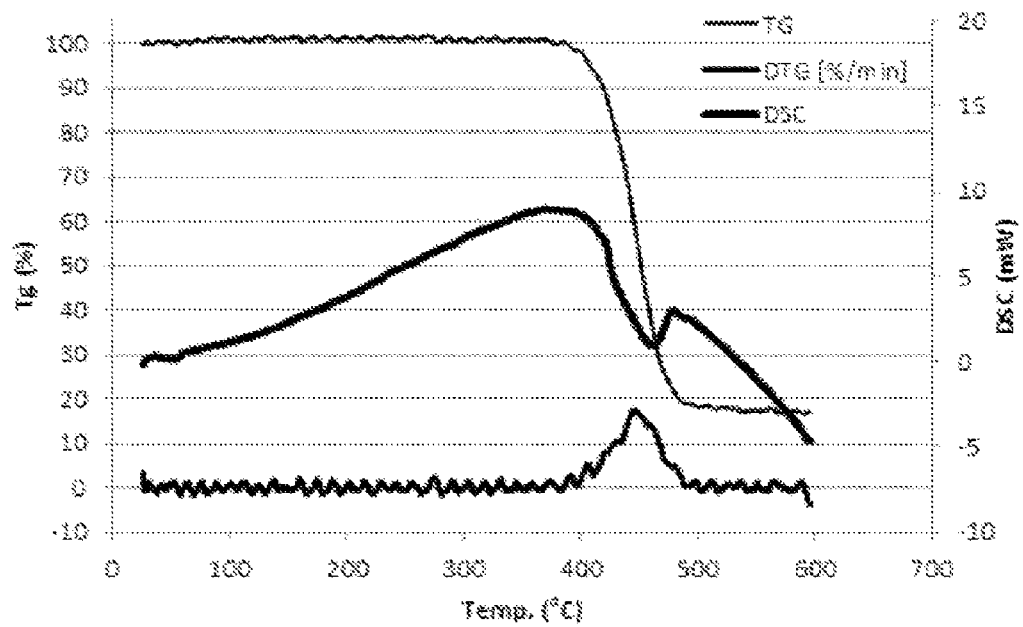
FIG. 23 shows that the polymeric poly[(3,7-diheptadecylthieno[3,2-b]thieno[2',3':4,5]thieno[2,3-d]thiophene-2,6-diyl) [2,5-d]heptadecyl-3,6-di(thiophen-2-yl)pyrrolo[3,4-c]pyrrole-1,4(2H,5H)-dione]-5,5'-diyl ("PTDC17DPPTDC17FT4") material was thermally stable to temperatures over 400° C. This is indicative of the stability of the polymer.

Fused thiophene based polymers such as P2TDC17FT4 have an upper mobility for charge transport (holes). This theoretical (and practical) limit may be raised by changing the polymer structure, replacing the bithiophene moiety with the mobility enhancing functionalized DPP moiety. The polymeric properties of PTDC17DPPTDC17FT4 are determined using standard testing methods. TGA measurements on the material show it is thermally stable up to 400° C. (FIG. 23) The TGA shows that the combination of the DPP moiety with the FT moiety unexpectedly provides a co-polymer that is highly stable relative to the DPP alone.

Figure 24:
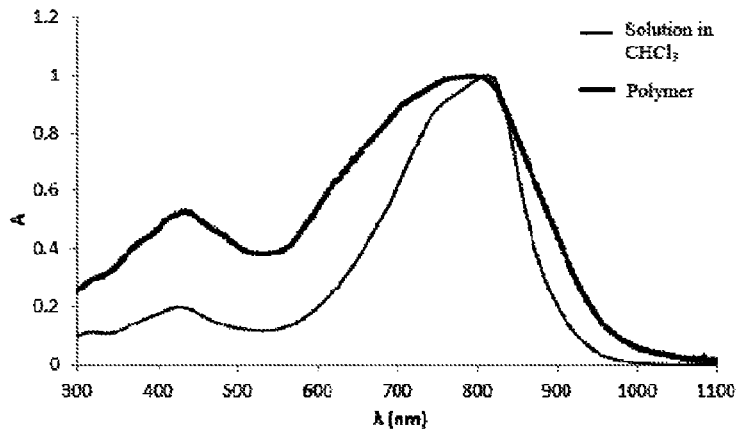
FIG. 24 shows UV-visible spectra of a chloroform solution and solid film of the PTDC17DPPTDC17FT4 polymer. Both species show a broad absorption from about 550 nm to about 950 nm and a less intense absorption from around 300 to 500 nm. These absorptions give the polymer a dark, almost green-black appearance which may be useful for photovoltaic systems.

The color of the new PTDC17DPPTDC17FT4 polymer is a very dark green, almost black, indicating a broad absorption across the visible region of the solar spectrum. UV-visible spectroscopy of both chloroform solution and thin film solid state spun from chloroform show a broad absorption from around 550 nm to around 950 nm and also a less intense absorption from around 300 nm to 500 nm (FIG. 24). This covers a very broad swath of the visible region and gives the polymer its dark green almost black appearance. One advantage of this material is its use in photovoltaic devices, where such broad solar absorption is desirable. Additionally, the extension of the absorption so far out into the IR is also highly desirable and is an unusual property when combined with absorptions as low at 300 nm in the same molecule. This makes the polymer more useful as the light absorber in an organic photovoltaic device, since light capture efficiency is a major contributor to photo-efficiency of a photovoltaic system. The strong light interaction also makes this material a suitable candidate for other optical and/or optoelectronic applications. Further, using bottom gate, top contact devices made on silicon wafer substrates as a common gate with a 300 nm thermal oxide dielectric layer and gold source and drain electrodes, compounds of structure PTDC16DPPTDC17FT4 show a hole mobility of greater than 2 $cm^2/V \cdot s$, an on/off ratio of greater than $10^6$ and a threshold voltage less than 2 V.

Example 12

Conjugated Polymers of Fused Thiophene Structures

Poly[(3,7-diheptadecylthieno[3,2-b]thieno[2',3':4,5]thieno[2,3-d]thiophene-2,6-diyl)(acetylene-1,2-diyl)] ("PTrDC17FT4") (FIG. 25)

2,6-dibromo-3,7-diheptadecylthieno[3,2-b]thieno[2',3':4,5]thieno[2,3-d]thiophene (0.41 g, 0.46 mmol) and Bis(tributylstannyl)acetylene (0.28 g, 0.462 mmol) are transferred into a three neck flask fitted with a stir bar. Nitrogen is bubbled through this flask for a few minutes. After the flask is sealed it is placed in a glovebox. 0.027 g (0.023 mmol) of Pd(PPh$_3$)$_4$ and a mixed solvent of 24 mL of anhydrous toluene and 6 mL of n-Butyl acetate are added to the flask. The flask is heated around 130° C. under nitrogen for 16 h before being poured into methanol (200 mL). The mixture is stirred overnight at room temperature. The precipitate is filtered and extracted in a Soxhlet, first with methanol for 24 h and then acetone for 24 h. The collected polymer is dried in vacuum to yield 0.18 grams of a dark polymer identified as poly[(3,7-diheptadecylthieno[3,2-b]thieno[2',3':4,5]thieno[2,3-d]thiophene-2,6-diyl)(acetylene-1,2-diyl)].

Poly[(3,7-diheptadecylthieno[3,2-b]thieno[2',3':4,5]thieno[2,3-d]thiophene-2,6-diyl)(vinylene-1,2-diyl)] ("PDouDC17FT4") (FIG. 26)

2,6-dibromo-3,7-diheptadecylthieno[3,2-b]thieno[2',3':4,5]thieno[2,3-d]thiophene (0.40 g, 0.45 mmol) and trans-1,2-Bis(tributylstannyl)ethylene (0.27 g, 0.45 mmol) are transferred into a three neck flask fitted with a stir bar. Nitrogen is bubbled through this flask for a few minutes. After the flask is sealed it is placed in a glovebox. 0.026 g (0.022 mmol) of Pd(PPh$_3$)$_4$ and 30 mL of anhydrous toluene are added to the flask. The flask is heated around 130° C. under nitrogen for 16 h before being poured into methanol (200 mL) and concentrated hydrochloric acid (5 mL) solution. The mixture is stirred overnight at room temperature. The precipitate is filtered and extracted in a Soxhlet, first with acetone for overnight and then hexane for overnight. The collected polymer is dried in vacuum to yield 0.29 grams of a blue polymer identified as poly[(3,7-diheptadecylthieno[3,2-b]thieno[2',3':4,5]thieno[2,3-d]thiophene-2,6-diyl)(vinylene-1,2-diyl)].

Poly[(3,7-diheptadecylthieno[3,2-b]thieno[2',3':4,5]thieno[2,3-d]thiophene-2,6-diyl)(2,1,3-benzothiadiazole-4,7-diyl)] ("P2BTDC17FT4") (FIG. 27)

2,6-dibromo-3,7-diheptadecylthieno[3,2-b]thieno[2',3':4,5]thieno[2,3-d]thiophene (1.00 g, 0.94 mmol) and 4,7-Dibromobenzo[c]-1,2,5-thiadiazole (0.28 g, 0.94 mmol) are transferred into a three neck flask fitted with a stir bar. Nitrogen is bubbled through this flask for a few minutes. After the flask is sealed it is placed in a glovebox. 0.055 g of Pd(PPh$_3$)$_4$ and 30 mL of anhydrous chlorobenzene are added to the flask. The flask is heated to around 130° C. under nitrogen for 16 h before being poured into methanol (200 mL) and concentrated hydrochloric acid (5 mL) solution. The mixture is stirred overnight at room temperature. The precipitate is filtered and extracted in a Soxhlet, first with acetone for overnight and then hexane for overnight. The collected polymer is dried in vacuum to yield 0.78 grams of a blue polymer identified as poly[(3,7-diheptadecylthieno[3,2-b]thieno[2',3':4,5]thieno[2,3-d]thiophene-2,6-diyl)(2,1,3-benzothiadiazole-4,7-diyl)]. ($\lambda_{max}$ in CHCl$_3$ solution=362 nm and 511 nm, $\lambda_{max}$ in thin film=511 nm and 578 nm. GPC (1,2,4-trichlorobenzene) Mn=8,200, Mw=9,400; and PDI=1.44).

It will be apparent to those skilled in the art that various modifications and variations can be made to the present description without departing from the spirit and scope. Thus, it is intended that the present description cover modifications and variations of embodiments herein provided they come within the scope of the appended claims and their equivalents.

What is claimed is:

1. A compound comprising the formula 100 or 101:

<chemical structure 100>

<chemical structure 101> wherein a, m, and n are independently integers of one or greater;
each X independently comprises a conjugated group, wherein a>1 and X is not aryl or heteroaryl; and
R$_1$ and R$_2$ are, independently, substituted or unsubstituted alkyl, substituted or unsubstituted alkenyl, substituted or unsubstituted alkynyl, aryl, substituted or unsubstituted cycloalkyl, aralkyl, amino, ester, aldehyde, hydroxyl, alkoxy, thiol, thioalkyl, halide, acyl halide, acrylate, or vinyl ether.

2. The compound of claim 1, wherein the compound comprises a polymer.

3. The compound of claim 1, wherein at, least one of R$_1$ and R$_2$ comprises a substituted or unsubstituted alkyl.

4. The compound of claim 3, wherein at least one of R$_1$ and R$_2$ comprises an unsubstituted alkyl.

5. The compound of claim 1, wherein a is 2 or more and X comprises a conjugated alkenyl or alkynyl.

6. The compound of claim 1, wherein the compound is incorporated into a conjugated fused thiophene polymer or oligomer having m>1.

7. The compound of claim 1, wherein n is from 1 to 15.

8. A polymer comprising the compound of claim 1, wherein the polymer has a molecular weight from about 400 to about 1800 Da.

9. A device comprising the compound of claim 1 configured in an electronic, optoelectronic, or nonlinear optical device.

10. The device of claim 9, wherein the device comprises a transistor (FET), a thin-film transistor (TFT), an organic light-emitting diode (OLED), an electro-optic (EO) device, a conductive material, a two photon mixing material, an organic semiconductor, a RFID tag, an electroluminescent device, or a photovoltaic and sensor device.

11. A method for making a compound of claim 1, comprising the steps of:
(i) providing a fused thiophene moiety of structure 1 or 2:

<chemical structure 1>

<chemical structure 2> wherein R$_1$ and R$_2$ independently, substituted or unsubstituted alkyl, substituted or unsubstituted alkenyl, substituted or unsubstituted alkynyl, aryl, substituted or unsubstituted cycloalkyl, aralkyl, amino, ester, aldehyde, hydroxyl, alkoxy, thiol, thioalkyl, halide, acyl halide, acrylate, or vinyl ether; and X and Y are independently, halide or Sn(Alk)$_3$, wherein Alk is a substituted or unsubstituted alkyl or substituted or unsubstituted cycloalkyl;

(ii) providing a bis-substituted conjugated moiety of structure 3 or 4:

$$Sn(Alk)_3\text{-}Z\text{—}Sn(Alk)_3 \quad\quad 3$$

$$Ha\text{-}Z\text{-}Ha \quad\quad 4$$

wherein Z is a conjugated group comprised no aryl or heteroaryl, Ha is halogen, and Alk is a substituted or unsubstituted alkyl or substituted or unsubstituted cycloalkyl;

(iii) coupling the fused thiophene moiety of structure 1 or 2 with the conjugated moiety of structure 3 or 4 via a catalyzed reaction; wherein compound 3 is used when X and Y are halogen and compound 4 is used when X and Y are Sn(Alk)$_3$.

12. The method of claim 11, wherein the catalyzed reaction is a metal catalyzed reaction.

13. The method of claim 12, wherein the metal catalyzed reaction is a Stille-type coupling.

14. The method of claim 11, further comprising polymerizing the compound of formula 100 or 101.

* * * * *